(12) United States Patent
Or

(10) Patent No.: US 7,910,558 B2
(45) Date of Patent: *Mar. 22, 2011

(54) BRIDGED MACROCYCLIC COMPOUNDS AND PROCESSES FOR THE PREPARATION THEREOF

(75) Inventor: Yat Sun Or, Watertown, MA (US)

(73) Assignee: Enanta Pharmaceuticals, Inc., Watertown, MA (US)

(*) Notice: Subject to any disclaimer, the term of this patent is extended or adjusted under 35 U.S.C. 154(b) by 838 days.

This patent is subject to a terminal disclaimer.

(21) Appl. No.: 10/763,377

(22) Filed: Jan. 23, 2004

(65) Prior Publication Data

US 2005/0009761 A1 Jan. 13, 2005

Related U.S. Application Data

(63) Continuation-in-part of application No. 10/429,485, filed on May 5, 2003, now Pat. No. 6,878,691, which is a continuation-in-part of application No. 10/144,558, filed on May 13, 2002, now abandoned, application No. 10/763,377, which is a continuation-in-part of application No. 10/436,622, filed on May 13, 2003, now Pat. No. 7,129,221, which is a continuation-in-part of application No. 10/144,396, filed on May 13, 2002, now abandoned, application No. 10/763,377, which is a continuation-in-part of application No. 10/205,018, filed on Jul. 25, 2002, now Pat. No. 6,841,664, and a continuation-in-part of application No. 10/205,357, filed on Jul. 25, 2002, now Pat. No. 6,753,318, and a continuation-in-part of application No. 10/464,188, filed on Jun. 18, 2003, now Pat. No. 6,764,998, and a continuation-in-part of application No. 10/668,688, filed on Sep. 23, 2003.

(51) Int. Cl.
*C07H 17/08* (2006.01)
*A61K 31/7048* (2006.01)

(52) U.S. Cl. .......................... 514/28; 536/7.1
(58) Field of Classification Search ................ 514/28; 536/7.1
See application file for complete search history.

(56) References Cited

U.S. PATENT DOCUMENTS

| | | | |
|---|---|---|---|
| 3,417,077 A | 12/1968 | Murphy et al. | |
| 4,990,602 A | 2/1991 | Morimoto et al. | |
| 5,403,923 A | 4/1995 | Kashimura et al. | |
| 5,444,051 A | 8/1995 | Agouridas et al. | |
| 5,527,780 A | 6/1996 | Agouridas et al. | |
| 5,631,355 A | 5/1997 | Asaka et al. | |
| 5,780,605 A * | 7/1998 | Or et al. ................ | 536/7.2 |
| 5,866,549 A | 2/1999 | Or et al. | |
| 5,922,683 A * | 7/1999 | Or et al. ................ | 514/29 |
| 5,969,161 A | 10/1999 | Bonnet et al. | |
| 6,046,171 A * | 4/2000 | Or et al. ................ | 514/29 |
| 6,054,435 A * | 4/2000 | Or et al. ................ | 514/29 |
| 6,075,133 A * | 6/2000 | Or et al. ................ | 536/7.2 |
| 6,124,269 A | 9/2000 | Phan et al. | |
| 6,274,715 B1 * | 8/2001 | Or et al. ................ | 536/7.4 |
| 6,355,620 B1 * | 3/2002 | Ma et al. ................ | 514/29 |
| 6,399,582 B1 | 6/2002 | Hlasta et al. | |
| 6,645,941 B1 * | 11/2003 | Wang et al. ................ | 514/29 |
| 6,753,318 B1 | 6/2004 | Or et al. | |
| 6,764,998 B1 * | 7/2004 | Wang et al. ................ | 514/29 |
| 6,878,691 B2 * | 4/2005 | Or et al. ................ | 514/29 |
| 2004/0053861 A1 | 3/2004 | Or et al. | |
| 2004/0157787 A1 | 8/2004 | Or et al. | |
| 2004/0171818 A1 | 9/2004 | Xu et al. | |
| 2004/0266998 A1 | 12/2004 | Or et al. | |
| 2005/0009763 A1 | 1/2005 | Or et al. | |
| 2005/0014707 A1 | 1/2005 | Wang et al. | |
| 2005/0159370 A1 | 7/2005 | Or et al. | |
| 2005/0171033 A1 | 8/2005 | Qiu et al. | |

FOREIGN PATENT DOCUMENTS

| | | |
|---|---|---|
| EP | 0 238 178 A1 | 9/1987 |
| WO | WO 99/21864 * | 5/1999 |
| WO | WO 00/78773 A2 | 12/2000 |
| WO | WO 01/00582 A1 | 1/2001 |
| WO | WO 01/14397 | 3/2001 |
| WO | WO 01/77134 A2 | 10/2001 |
| WO | WO 03/042228 | 5/2003 |
| WO | WO 03/095466 A1 | 11/2003 |
| WO | WO 03/097659 A1 | 11/2003 |

OTHER PUBLICATIONS

U.S. Appl. No. 11/154,260, filed Jun. 16, 2005, Deqiang Niu et al.
U.S. Appl. No. 11/029,640, filed Jan. 5, 2005, Nha Huu Vo, et al.
U.S. Appl. No. 11/057,476, filed Feb. 14, 2005, Datong Tang, et al.
U.S. Appl. No. 11/122,251, filed May 4, 2005, Guoqiang Wang, et al.
8th International Antibacterial Drug Discovery and Development Summit, *Strategic Research Institute*, Mar. 24-25, 2003, Princeton, NJ. Corey, E.J., and Kim, C.U., "A New and Highly Effective Method for the Oxidation of Primary and Secondary Alcohols to Carbonyl Compounds," *J. American Chemical Society*, 94(21): 7586 (1972).
U.S. Appl. No. 10/429,485, filed May 5, 2003, Yat Sun Or et al.
U.S. Appl. No. 10/436,622, filed May 13, 2003, Yat Sun Or et al.
U.S. Appl. No. 10/205,018, filed Jul. 25, 2002, Yat Sun Or et al.
U.S. Appl. No. 11/257,680, filed Oct. 25, 2005, Wang et al.

* cited by examiner

*Primary Examiner* — Shaojia Anna Jiang
*Assistant Examiner* — Ganapathy Krishnan
(74) *Attorney, Agent, or Firm* — Carolyn S. Elmore, Esq.; Edgar W. Harlan; Elmore Patent Law Group, P.C.

(57) ABSTRACT

The present invention provides a method for preparing bridged macrocyclic compounds comprising the step of reacting a macrocyclic compound characterized by having at least two nucleophilic moieties with a bifunctional bridging reagent optionally in the presence of a catalyst, thereby producing a bridged macrocyclic product.

13 Claims, No Drawings

BRIDGED MACROCYCLIC COMPOUNDS AND PROCESSES FOR THE PREPARATION THEREOF

RELATED APPLICATIONS

This application is a continuation-in-part of U.S. Application Ser. No. 10/429,485, filed May 5, 2003, now U.S. Pat. No. 6,878,691 which is continuation-in-part of U.S. application Ser. No. 10/144,558, filed May 13, 2002, now abandoned; a continuation-in-part of U.S. application Ser. No. 10/436,622, filed May 13, 2003, now U.S. Pat. No. 7,129,221 which is a continuation-in-part of U.S. application Ser. No. 10/144,396, filed May 13, 2002, now abandoned; a continuation-in-part of U.S. application Ser. No. 10/205,018, filed Jul. 25, 2002; now U.S. Pat. No. 6,841,664 a continuation-in-part of U.S. application Ser. No. 10/205,357, filed Jul. 25, 2002; now U.S. Pat. No. 6,753,318 a continuation-in-part of U.S. application Ser. No. 10/464,188, filed Jun. 18, 2003; now U.S. Pat. No. 6,764,998 and a continuation-in-part of U.S. application Ser. No. 10/668,688, filed Sep. 23, 2003, which are all incorporated herein by reference. This application is also related to U.S. Pat. No. 6,645,941, which is incorporated herein by reference.

TECHNICAL FIELD

The present invention relates to a method of producing bridged macrocyclic compounds

BACKGROUND OF THE INVENTION

Macrolide antibiotics play a therapeutically important role, particularly with the emergence of new pathogens. Structural differences are related to the size of the lactone ring and to the number and nature (neutral or basic) of the sugars. Macrolides are classified according to the size of the lactone ring (12, 14, 15 or 16 atoms). The macrolide antibiotic family (14-, 15- and 16-membered ring derivatives) shows a wide range of characteristics (antibacterial spectrum, side-effects and bioavailability). Among the commonly used macrolides are erythromycin, clarithromycin, and azithromycin. Macrolides possessing a 3-oxo moiety in place of the 3-cladinose sugar are known as ketolides and have shown enhanced activity towards gram-negative bacteria and macrolide resistant gram-positive bacteria. The search for macrolide compounds which are active against $MLS_B$-resistant strains ($MLS_B$=Macrolides-Lincosamides-type B Streptogramines) has become a major goal, together with retaining the overall profile of the macrolides in terms of stability, tolerance and pharmacokinetics.

SUMMARY OF THE INVENTION

The present invention provides a method for preparing bridged macrocyclic compounds comprising the step of reacting a macrocyclic compound characterized by having at least two nucleophilic moieties with a bifunctional bridging reagent optionally in the presence of a catalyst, thereby producing a bridged macrocyclic product.

Another embodiment of the present invention is the bridged macrocyclic compounds produced by the process and libraries comprising such compounds.

DETAILED DESCRIPTION OF THE INVENTION

The process of the present invention is suitable for the preparation of bridged macrocyclic compounds from macrocyclic compounds.

Macrocyclic compounds useful in the process of the present invention are cyclic compounds comprising at least 7 ring atoms selected from carbon, nitrogen, oxygen, sulfur, silicon, phosphorous, or other atoms, wherein each ring atom may optionally be substituted with oxygen, and each macrocyclic compound may optionally contain one or more degrees of unsaturation (double or triple bonds). It is understood that the macrocyclic compounds useful in the present invention can be multicyclic, such as bi- or tricyclic. It also is understood that the macrocyclic compounds of the present invention will contain at least two nucleophilic moieties and may be substituted with one or more aromatic or aliphatic substituents. The nucleophilic moieties may themselves be a ring atom or may be a substituent attached to a ring atom. Preferred nucleophilic moieties include, but are not limited to, hydroxy, amine, imine, oxime, thiol, hydrazine, and the like.

Preferred macrocyclic compounds useful in the process of the present invention are macrolides. Macrolides which are suitable for the process of the present invention include but are not limited to, methymycin, neomethymycin, YC-17, litorin, erythromycins, oleandomycins, sporeamycin, dirithromycin, flurithromycin, davercin, ER 42859, A-69334, A-77113, A-69230. A-69730, A-66991, A-70310, A-75729, roxithromycin, telithromycin, cethromycin, azithromycin, megalomicins, narbomycin, pikromycin, dihydropikromycin, kujimycins, lankamycins, leucomycins, platenomycins, midecamycins, maridomycin complex, carbomycins, niddamycins, juvenimicins, M4365 $G_1$, M-4365 $G_2$, tylosin, relomycin, macrocin deltamycin complex, cirramycin, acumycin, rosaramicin, M-4365 $A_1$, M-6888-C, M-6888-X, anglomycin, staphococcomycin, spiramycin, mycinamicin I, mycinamicin II, mycinamicin III, mycinamicin IV, mycinamicin V, mycinamicin VI, mycinamicin VII, mycinamicin VIII, chalcomycin, neutromycin, aldgamycins, swalpamycin, rokitamycin, kitasamycin, octalactins, juglorubin, nargenicin, spinosyns, SCH 23831, avermectins, lankacidins, concanamycins, venturicidins, cytovaricin, maduralide, ossamycin, oligomycins, izumenolide, dotriacolide, sporaviridins, guanadylfungins, malolactomycins, RP 63834, desertomycins, oasomycins, monazomycins, apoptolidin, labilomycin, quinolidomycins, lucensomysin, rimocidin, nystatins, aurenin, filipin III, roxaticin, flavofungin I, roflamycoin, lienomycin, dermostatins, amphotericins, antimycins, elaiophylin, pamamycin-607, actinoplanic acid, boromycin, neoantimycin, nonactin, tacrolimus, viridenomycin, vancomycins, rapamycins, leucomycins, josamycins, FK506, rifamycins, and the like, as well as their homologs, analogs, and derivatives, either of natural or synthetic origin (see Omura, Satoshi, ed., *MACROLIDE ANTIBIOTICS: Chemistry, Biology, and Practice*, Academic Press (2002); Schonfeld, W. & Kirst, H. A., eds. *MILESTONES IN DRUG THERAPY: Macrolide Antibiotics*, Birkhauser Verlag (2002); and Bryskier, A. J., Butzler, J.-P, Neu, H. C. & Tulkens, P. M., eds. *MACROLIDES: Chemistry, Pharmacology, and Clinical Uses*, Arnette Blackwell (1993), which are all incorporated herein by reference).

Macrocyclic compounds useful in the process of the instant invention include, but are not limited to:
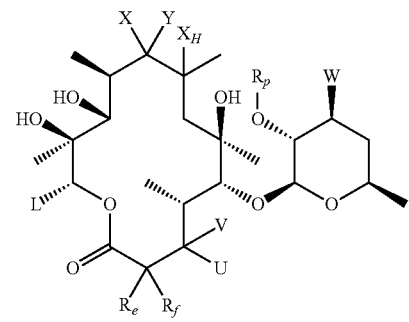
I
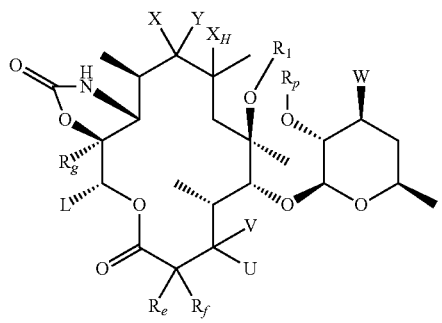
V
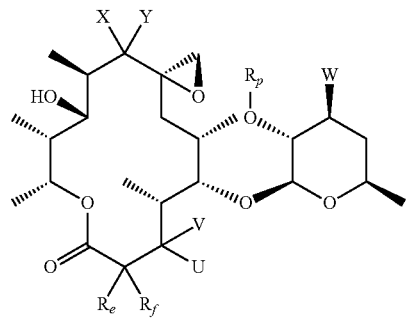
II
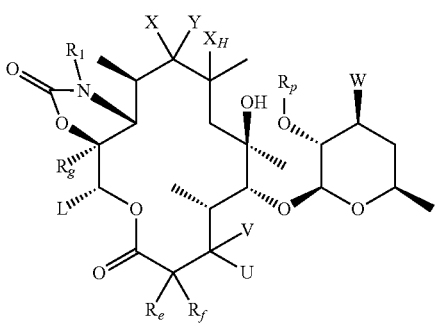
VI
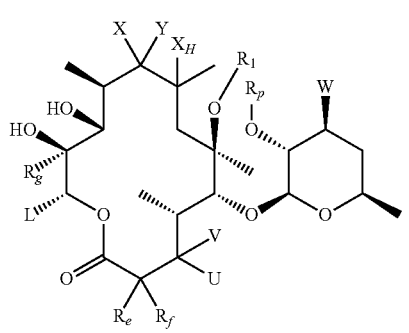
III
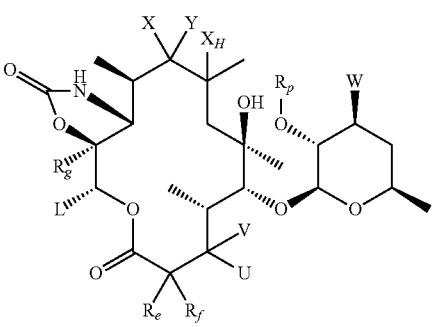
VII
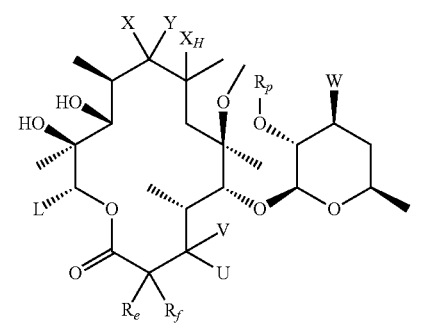
VIII
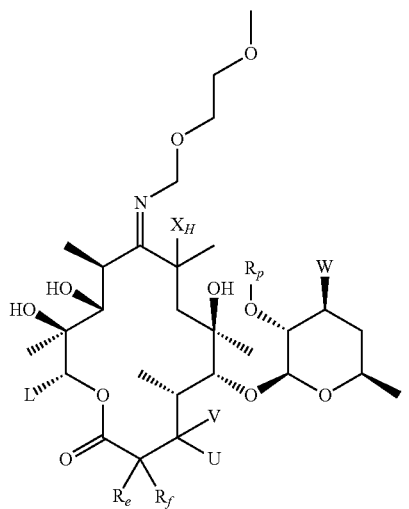
IV
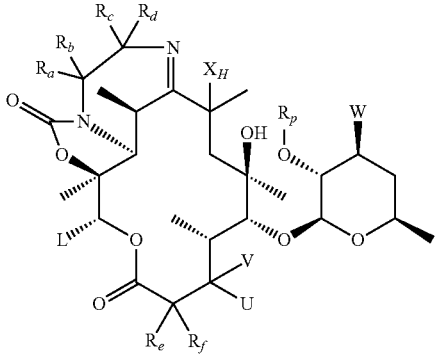
IX -continued

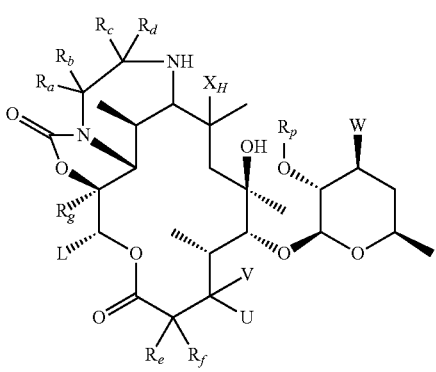
X

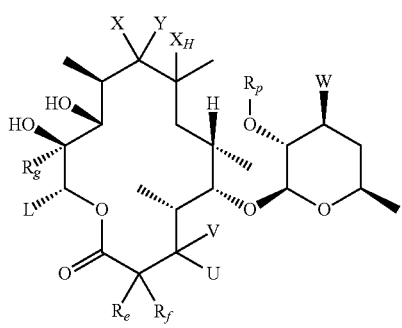
XI

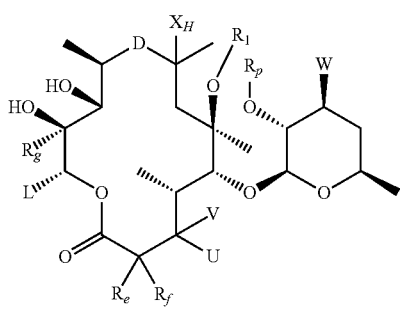
XII

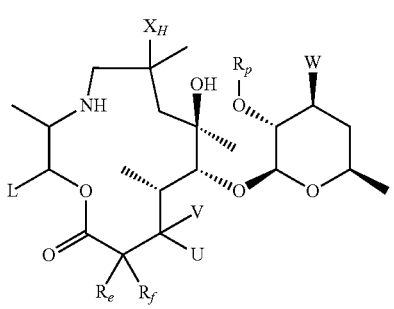
XIII

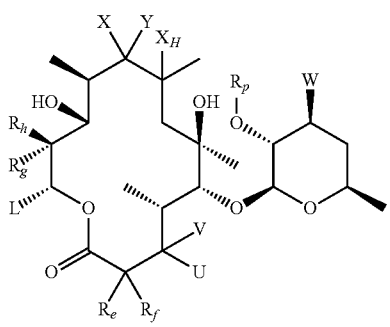
XIV wherein
D is selected from —NHCH$_2$—, —NHCHR$_1$—, —NHCR$_3$R$_4$—, —NR$_1$CH$_2$—, —NHC(O)—, —NR$_1$C(O)—, —NHC(S)—, or —NR$_1$C(S)—;

Each R$_1$ is independently selected from hydrogen, deuterium, a substituted or unsubstituted, saturated or unsaturated aliphatic group, a substituted or unsubstituted, saturated or unsaturated alicyclic group, a substituted or unsubstituted aromatic group, a substituted or unsubstituted heteroaromatic group, saturated or unsaturated heterocyclic group;

R$_3$ and R$_4$ is independently selected from the group consisting of hydrogen, acyl, a substituted or unsubstituted, saturated or unsaturated aliphatic group, a substituted or unsubstituted, saturated or unsaturated alicyclic group, a substituted or unsubstituted aromatic group, a substituted or unsubstituted heteroaromatic group, saturated or unsaturated heterocyclic group; or can be taken together with the nitrogen atom to which they are attached to form a substituted or unsubstituted heterocyclic or heteroaromatic ring;

L is selected from hydrogen, a substituted or unsubstituted, saturated or unsaturated aliphatic group, a substituted or unsubstituted, saturated or unsaturated alicyclic group, a substituted or unsubstituted aromatic group, a substituted or unsubstituted heteroaromatic group, or a substituted or unsubstituted heterocyclic group;
preferably L can be ethyl;

one of U or V is hydrogen and the other is independently selected from the group consisting of: R$_1$, OR$_1$, OC(O)R$_1$, OC(O)NR$_3$R$_4$, S(O)$_n$R$_1$, or other carbohydrate or sugar moiety;
or U and V, taken together with the carbon atom to which they are attached, are C=O;
or UV and R$_e$R$_f$ taken together with the carbon atoms to which they are attached, are —C(R$_1$)=CH—;
one of J or G is hydrogen and the other is selected from: R$_1$, OR$_1$, or NR$_3$R$_4$;
or J and G, taken together with the carbon atom to which they are attached, are selected from: C=O, C=NR$_1$, C=NOR$_1$, C=NO(CH$_2$)$_m$R$_1$, C=NNHR$_1$, C=NNHCOR$_1$, C=NNHCONR$_3$R$_4$, C=NNHS(O)$_n$R$_1$, or C=N—N=CHR$_1$;

R$_a$, R$_b$, R$_c$, and R$_d$ are independently selected from —R$_1$, —OR$_1$, —S(O)$_n$R$_1$, —C(O)OR$_1$, —OC(O)R$_1$, —OC(O)OR$_1$, —C(O)R$_1$, —C(O)NH—R$_1$, —NHC(O)—R$_1$, —N(R$_3$)(R$_4$), —NHC(O)—OR$_1$, —NHC(O)NH—R$_1$, or —OC(O)NH—R$_1$;

or R$_a$ and R$_b$, R$_a$ and R$_c$, R$_a$ and R$_d$, R$_b$ and R$_c$, R$_b$ and R$_d$, or R$_c$ and R$_d$, taken together with the carbon atom or atoms to which they are attached, are selected from substituted or unsubstituted alicyclic or substituted or unsubstituted heterocyclic;

one of R$_e$ and R$_f$ is selected from hydrogen or methyl, and the other is independently selected from halogen, deuterium, or R$_1$.

preferably one of $R_e$ and $R_f$ can be methyl and the other is halogen, or one of $R_e$ and $R_f$ can be hydrogen and the other is selected from methyl, allyl, or propargyl;

$R_h$ is hydroxy;

$R_g$ is selected from hydrogen, a substituted or unsubstituted, saturated or unsaturated aliphatic group, a substituted or unsubstituted, saturated or unsaturated alicyclic group, a substituted or unsubstituted aromatic group, a substituted or unsubstituted heteroaromatic group, or a substituted or unsubstituted heterocyclic group;

preferably $R_g$ can be methyl;

or $R_g$ and $R_h$, taken together with the carbon atom to which they are attached, are selected from an epoxide, a carbonyl, a substituted or unsubstituted olefin, a substituted or unsubstituted alicyclic, a substituted or unsubstituted heterocyclic;

W is $NR_3R_4$;

one of X and Y is hydrogen, substituted or unsubstituted aliphatic, and the other is independently selected from: hydroxy, —SH, —$NH_2$, or —$NR_1H$;

or X and Y, taken together with the carbon atom to which they are attached, are selected from: C=O, C=$NR_1$, C=$NOR_1$, C=$NO(CH_2)_mR_1$, C=$NNHR_1$, C=$NNHCOR_1$, C=$NNHCONR_1R_2$, C=$NNHS(O)_nR_1$, or C=N—N=$CHR_1$;

preferably X and Y, taken together with the carbon atom to which they are attached, can be selected from C(O), C=NH, C=N—$NH_2$, or C=N—OH;

$R_p$ is selected from hydrogen or a hydroxy protecting group;

$X_H$ is selected from hydrogen or halogen;

m is an integer; and n is 0, 1, or 2.

It is understood that the forgoing compounds of formulas I-XIV are intended to be exemplary macrocyclic compounds, or intermediates or derivatives thereof, which are suitable for the process of the present invention.

Bifunctional bridging reagents which are useful in the instant invention are compounds of the formula

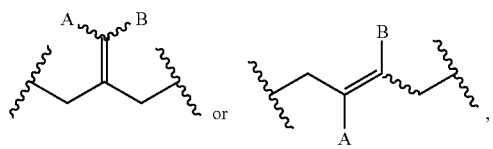

wherein Q is selected from

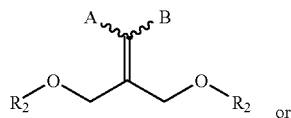

A and B are independently selected from hydrogen, deuterium, halogen, —Si($R_1$)$_3$, $R_1$, or $OR_1$, and $R_2$ is a hydroxy protecting group.

Preferred bifunctional bridging reagents of the present invention are of the formulas

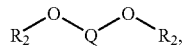

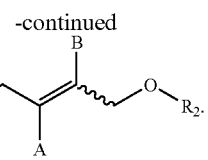

In a preferred embodiment, each $R_2$ is independently selected from —C(O)$OR_1$ or —Si($R_1$)$_3$. In a most preferred embodiment, each $R_2$ is —C(O)O(t-Butyl) or one $R_2$ is —C(O)O(t-Butyl) and one $R_2$ is TBS. Therefore, 2-, 3-, and 4-carbon bridged macrocyclic products are preferred products of the present invention.

In another embodiment of the present invention, the bridged macrocyclic product is a 6-11 3-carbon bridged erythromycin such as those of formula 1:

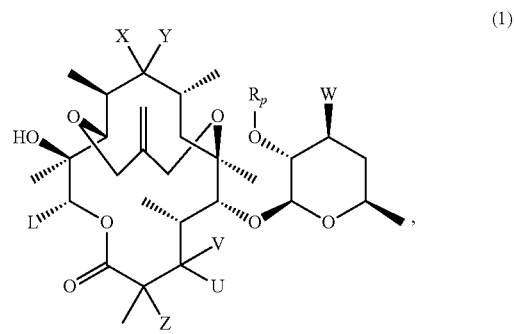

wherein Z is selected from hydrogen, methyl or halogen.

In another embodiment of the present invention, the bridged macrocyclic product is a 6-11 4C-bridged erythromycin, such as those of formula 2:

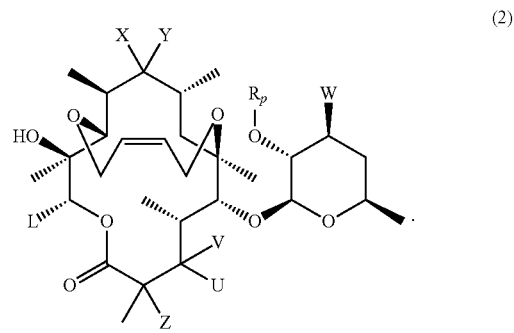

In an alternate embodiment of the present invention, the bridged macrocyclic product is not a compound of formulas (1) or (2).

The process of the present invention may occur in one step or in several steps. In one embodiment of the present invention, the reaction occurs in a concerted manner whereby a first nucleophilic moiety of the macrocyclic compound is alkylated by a first functional group of the bifunctional bridging reagent followed by a second nucleophilic moiety of the macrocyclic compound being alkylated by a second functional group of the bifunctional bridging moiety. In aother embodiment, the second functional group of the bifunctional bridging moiety may be altered after the alkylation of the first nucleophilic moiety of the macrocyclic compound and prior to the alkylation of the second nucleophilic moiety of the macrocyclic compound.

Catalysts which are suitable for the process of the present invention are metal catalysts which are capable of undergoing oxidative addition/insertion to form a π-allyl-metal complex. Preferred metals suitable for the formation of π-allyl-metal complexes include, but are not limited to, palladium, nickel, or molybdenum. More preferably, the catalyst useful in the process of the present invention is a palladium catalyst. The palladium catalyst can be a palladium(II) or a palladium(0) catalyst.

In addition, the process of the present invention is preferably performed in the presence of a ligand. Examples of preferred ligands include arsines or monodentate phosphorus-containing ligands of formulas $P(R_C)_3$ (phosphines), and $P(OR_D)_3$ (phosphites), wherein each $R_C$ is independently hydrogen; alkyl such as methyl, ethyl, propyl and butyl, such as tert-butyl; cycloalkyl such as cyclopropyl, cyclobutyl, cyclopentyl and cyclohexyl and unsaturated derivatives thereof; substituted or unsubstituted aryl, such as phenyl, naphthyl, and tolyl; and substituted or unsubstituted heteroaryl such as furyl and pyridyl; and wherein each $R_D$ is independently alkyl such as methyl, ethyl, propyl and butyl, such as tert-butyl; cycloalkyl, such as cyclopropyl, cyclobutyl, cyclopentyl and cyclohexyl and unsaturated derivatives thereof; substituted or unsubstituted aryl, such as phenyl, naphthyl, and tolyl; and substituted or unsubstituted heteroaryl, such as furyl and pyridyl. Specific examples of ligands useful in the process of the present invention include, but are not limited to, tri(alkyl)phosphines such as trimethylphosphine, triethylphosphine, tributylphosphine, and the like; tri(cycloalkyl)phosphines such as tricyclopropylphosphine, tricyclohexylphosphine, and the like; tri(aryl)phosphines such as triphenylphosphine, trinaphthylphosphine, and the like; tri(heteroaryl)phosphines such as tri(fury-2-yl)phosphine, tri(pyrid-3-yl)phosphine, and the like; tri(alkyl)phosphites such as trimethylphosphite, triethylphosphite, tributylphosphite, and the like; tri(cycloalkyl)-phosphites such as tricyelopropylphosphite, tricyclohexylphosphite, and the like; tri(aryl)phosphites such as triphenylphosphite, trinaphthylphosphite, and the like; and tri(heteroaryl)phosphites such as tri(fury-2-yl)phosphite, tri(pyrid-3-yl)phosphite, and the like. Asymmetric ligands, such as dimethylbutyl phosphine, are also contemplated herein. Ligands suitable for the process of the present invention also include bidentate phosphines such as 1,4-bis(diphenylphosphino)butane (dppb), 1,2-bis(diphenyl-phosphino)ethane (dppe), 1,1-bis (diphenylphosphino)methane (dppm), 1,2-bis(dimethylphosphino)ethane (dmpe), 1,1'-bis(diphenylphosphino)ferrocene (dppf), and the like. A particularly preferred ligand of the instant process is 1,4-bis(diphenylphosphino)butane (dppb).

For further discussion of suitable palladium reaction conditions for the process of the present invention, see (a) Trost, B. M. *Angew. Chem. Int. Ed. Eng.* 1989, 28, 1179; (b) Heck, Palladium Reagents in Organic Synthesis, Academic Press: New York, 1985, Chapter 1; (c) Tsuji, *Tetrahedron Lett.* 1992, 33, 2987; (d) Beller et al. *Angew. Chem. Int. Ed. Engl.*, 1995, 34 (17), 1848, etc.

DEFINITIONS

Listed below are definitions of various terms used to describe this invention. These definitions apply to the terms as they are used throughout this specification and claims, unless otherwise limited in specific instances, either individually or as part of a larger group.

An "aliphatic group" is non-aromatic moiety that may contain any combination of carbon atoms, hydrogen atoms, halogen atoms, oxygen, nitrogen, sulfur or other atoms, and optionally contain one or more units of unsaturation, e.g., double and/or triple bonds. An aliphatic group may be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted.

Suitable aliphatic or aromatic substituents include, but are not limited to, —F, —Cl, —Br, —I, —OH, protected hydroxy, aliphatic ethers, aromatic ethers, oxo, —$NO_2$, —CN, —$C_1$-$C_{12}$-alkyl optionally substituted with halogen (such as perhaloalkyls), $C_2$-$C_{12}$-alkenyl optionally substituted with halogen, —$C_2$-$C_{12}$-alkynyl optionally substituted with halogen, —$NH_2$, protected amino, —NH—$C_1$-$C_{12}$-alkyl, —NH—$C_2$-$C_{12}$-alkenyl, —NH—$C_2$-$C_{12}$-alkenyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_{12}$-alkenyl, —O—$C_2$-$C_{12}$-alkynyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_{12}$-alkenyl, —C(O)—$C_2$-$C_{12}$-alkynyl, —C(O)—$C_3$-$C_{12}$-cycloalkyl, —C(O)-aryl, —C(O)-heteroaryl, —C(O)-heterocycloalkyl, —$CONH_2$, —CONH—$C_1$-$C_{12}$-alkyl, —CONH—$C_2$-$C_{12}$-alkenyl, —CONH—$C_2$-$C_{12}$-alkynyl, —CONH—$C_3$-$C_{12}$-cycloalkyl, —CONH-aryl, —CONH-heteroaryl, —CONH-heterocycloalkyl, —$CO_2$—$C_1$-$C_{12}$-alkyl, —$CO_2$—$C_2$-$C_{12}$-alkenyl, —$CO_2$—$C_2$-$C_{12}$-alkynyl, —$CO_2$—$C_3$-$C_{12}$-cycloalkyl, —$CO_2$-aryl, —$CO_2$-heteroaryl, —$CO_2$-heterocycloalkyl, —$OCO_2$—$C_1$-$C_{12}$-alkyl, —$OCO_2$—$C_2$-$C_{12}$-alkenyl, —$OCO_2$—$C_2$-$C_{12}$-alkynyl, —$OCO_2$—$C_3$-$C_{12}$-cycloalkyl, —$OCO_2$-aryl, —$OCO_2$-heteroaryl, —$OCO_2$-heterocycloalkyl, —$OCONH_2$, —OCONH—$C_1$-$C_{12}$-alkyl, —OCONH—$C_2$-$C_{12}$-alkenyl, —OCONH—$C_2$-$C_{12}$-alkynyl, —OCONH—$C_3$-$C_{12}$-cycloalkyl, —OCONH-aryl, —OCONH-heteroaryl, —OCONH-heterocycloalkyl, —NHC(O)—$C_1$-$C_{12}$-alkyl, —NHC(O)—$C_2$-$C_{12}$-alkenyl, —NHC(O)—$C_2$-$C_{12}$-alkynyl, —NHC(O)—$C_3$-$C_{12}$-cycloalkyl, —NHC(O)-aryl, —NHC(O)-heteroaryl, —NHC(O)-heterocycloalkyl, —$NHCO_2$—$C_1$-$C_{12}$-alkyl, —$NHCO_2$—$C_2$-$C_{12}$-alkenyl, —$NHCO_2$—$C_2$-$C_{12}$-alkynyl, —$NHCO_2$—$C_3$-$C_{12}$-cycloalkyl, —$NHCO_2$-aryl, —$NHCO_2$-heteroaryl, —$NHCO_2$-heterocycloalkyl, —NHC(O)$NH_2$, NHC(O)NH—$C_1$-$C_{12}$-alkyl, —NHC(O)NH—$C_2$-$C_{12}$-alkenyl, —NHC(O)NH—$C_2$-$C_{12}$-alkynyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)$NH_2$, NHC(S)NH—$C_1$-$C_{12}$-alkyl, —NHC(S)NH—$C_2$-$C_{12}$-alkenyl, —NHC(S)NH—$C_2$-$C_{12}$-alkynyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)$NH_2$, NHC(NH)NH—$C_1$-$C_2$-alkyl, —NHC(NH)NH—$C_2$-$C_{12}$-alkenyl, —NHC(NH)NH—$C_2$-$C_{12}$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, NHC(NH)—$C_1$-$C_{12}$-alkyl, —NHC(NH)—$C_2$-$C_{12}$-alkenyl, —NHC(NH)—$C_2$-$C_2$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_{12}$-alkenyl, —C(NH)NH—$C_2$-$C_{12}$-alkynyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_{12}$-alkenyl, —S(O)—$C_2$-$C_{12}$-alkynyl, —S(O)—$C_3$-$C_{12}$- cycloalkyl, —S(O)-aryl, —S(O)-heteroaryl, —S(O)-heterocycloalkyl —$SO_2NH_2$, —$SO_2NH$—$C_1$-$C_{12}$-alkyl, —$SO_2NH$—$C_2$-$C_{12}$-alkenyl, —$SO_2NH$—$C_2$-$C_{12}$-alkynyl, —$SO_2NH$—$C_3$-$C_{12}$-cycloalkyl, —$SO_2NH$-aryl, —$SO_2NH$-heteroaryl, —$SO_2NH$-heterocycloalkyl, —$NHSO_2$—$C_1$-$C_{12}$-alkyl, —$NHSO_2$—$C_2$-$C_{12}$-alkenyl, —$NHSO_2$—$C_2$-$C_{12}$-alkynyl, —$NHSO_2$—$C_3$-$C_2$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_{12}$-alkenyl, —S—$C_2$-$C_{12}$-alkynyl, —S—$C_3$-$C_{12}$-cycloalkyl, —S-aryl, —S-heteroaryl, —S-heterocycloalkyl, or methylthiomethyl. It is understood that the aryls, heteroaryls, alkyls and the like can be further substituted.

The terms "$C_2$-$C_{12}$ alkenyl" or "$C_2$-$C_6$ alkenyl," as used herein, denote a monovalent group derived from a hydrocarbon moiety containing from two to twelve or two to six carbon atoms having at least one carbon-carbon double bond by the removal of a single hydrogen atom. Alkenyl groups include, but are not limited to, for example, ethenyl, propenyl, butenyl, 1-methyl-2-buten-1-yl, alkadienes and the like.

The term "substituted alkenyl," as used herein, refers to a "$C_2$-$C_{12}$ alkenyl" or "$C_2$-$C_6$ alkenyl" group as previously defined, substituted by one, two, three or more aliphatic substituents.

The terms "$C_2$-$C_{12}$ alkynyl" or "$C_2$-$C_6$ alkynyl," as used herein, denote a monovalent group derived from a hydrocarbon moiety containing from two to twelve or two to six carbon atoms having at least one carbon-carbon triple bond by the removal of a single hydrogen atom. Representative alkynyl groups include, but are not limited to, for example, ethynyl, 1-propynyl, 1-butynyl, and the like.

The term "substituted alkynyl," as used herein, refers to a "$C_2$-$C_{12}$ alkynyl" or "$C_2$-$C_6$ alkynyl" group as previously defined, substituted by one, two, three or more aliphatic substituents.

The term "$C_1$-$C_6$ alkoxy," as used herein, refers to a $C_1$-$C_6$ alkyl group, as previously defined, attached to the parent molecular moiety through an oxygen atom. Examples of $C_1$-$C_6$-alkoxy include, but are not limited to, methoxy, ethoxy, propoxy, isopropoxy, n-butoxy, sec-butoxy, tert-butoxy, n-pentoxy, neopentoxy and n-hexoxy.

The terms "halo" and "halogen," as used herein, refer to an atom selected from fluorine, chlorine, bromine and iodine.

The terms "aryl" or "aromatic" as used herein, refer to a mono- or bicyclic carbocyclic ring system having one or two aromatic rings including, but not limited to, phenyl, naphthyl, tetrahydronaphthyl, indanyl, idenyl and the like.

The terms "substituted aryl" or "substituted aromatic," as used herein, refer to an aryl or aromatic group substituted by one, two, three or more aromatic substituents.

The term "arylalkyl," as used herein, refers to an aryl group attached to the parent compound via a $C_1$-$C_3$ alkyl or $C_1$-$C_6$ alkyl residue. Examples include, but are not limited to, benzyl, phenethyl and the like.

The term "substituted arylalkyl," as used herein, refers to an arylalkyl group, as previously defined, substituted by one, two, three or more aromatic substituents.

The terms "heteroaryl" or "heteroaromatic," as used herein, refer to a mono-, bi-, or tri-cyclic aromatic radical or ring having from five to ten ring atoms of which at least one ring atom is selected from S, O and N; zero, one or two ring atoms are additional heteroatoms independently selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. The heteroaromatic ring may be bonded to the chemical structure through a carbon or hetero atom.

The terms "substituted heteroaryl" or "substituted heteroaromatic," as used herein, refer to a heteroaryl or heteroaromatic group, substituted by one, two, three, or more aromatic substituents.

The term "alicyclic," as used herein, denotes a monovalent group derived from a monocyclic or bicyclic saturated carbocyclic ring compound by the removal of a single hydrogen atom. Examples include, but are not limited to, cyclopropyl, cyclobutyl, cyclopentyl, cyclohexyl, bicyclo [2.2.1]heptyl, and bicyclo [2.2.2]octyl.

The term "substituted alicyclic," as used herein, refers to an alicyclic group substituted by one, two, three or more aliphatic substituents.

The term "heterocyclic," as used herein, refers to a non-aromatic ring, comprising three or more ring atoms, or a bi- or tri-cyclic group fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, (iv) any of the above rings may be fused to a benzene ring, and (v) the remaining ring atoms are carbon atoms which may be optionally oxo-substituted. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, and tetrahydrofuryl.

The term "substituted heterocyclic," as used herein, refers to a heterocyclic group, as previously defined, substituted by one, two, three or more aliphatic substituents.

The term "heteroarylalkyl," as used herein, to an heteroaryl group attached to the parent compound via a $C_1$-$C_3$ alkyl or $C_1$-$C_6$ alkyl residue. Examples include, but are not limited to, pyridinylmethyl, pyrimidinylethyl and the like.

The term "substituted heteroarylalkyl," as used herein, refers to a heteroarylalkyl group, as previously defined, substituted by independent replacement of one, two, or three or more aromatic substituents.

The term "alkylamino" refers to a group having the structure —$NH(C_1$-$C_{12}$ alkyl).

The term "dialkylamino" refers to a group having the structure —$N(C_1$-$C_{12}$ alkyl) ($C_1$-$C_{12}$ alkyl), and cyclic amines. Examples of dialkylamino are, but not limited to, dimethylamino, diethylamino, methylethylamino, piperidino, morpholino and the like.

The term "alkoxycarbonyl" represents an ester group, i.e., an alkoxy group, attached to the parent molecular moiety through a carbonyl group such as methoxycarbonyl, ethoxycarbonyl, and the like.

The term "carboxaldehyde," as used herein, refers to a group of formula —CHO.

The term "carboxy," as used herein, refers to a group of formula —COOH.

The term "carboxamide," as used herein, refers to a group of formula —$C(O)NH(C_1$-$C_{12}$ alkyl) or —$C(O)N(C_1$-$C_{12}$ alkyl) ($C_1$-$C_{12}$ alkyl), —$C(O)NH_2$, $NHC(O)(C_1$-$C_{12}$ alkyl), $N(C_1$-$C_{12}$ alkyl)$C(O)(C_1$-$C_{12}$ alkyl) and the like.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the are described generally in T. H. Greene and P. G. M. Wuts, *Protective Groups in Organic Synthesis,* 3rd edition, John Wiley & Sons, New York (1999). Examples of hydroxyl protecting groups include benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, 1,1-dimethyl-2-propenyl, 3-methyl-3-butenyl, allyl, benzyl, para-methoxybenzyldiphenylmethyl, triphenylmethyl(trityl), tetrahydrofuryl, methoxymethyl, methylthiomethyl, benzyloxymethyl, 2,2,2-triehloroethoxymethyl, 2-(trimethylsilyl)ethoxymethyl, methanesulfonyl, para-toluenesulfonyl, trimethylsilyl, triethylsilyl, triisopropylsilyl, and the like. Preferred hydroxyl protecting groups for the present invention are acetyl (Ac or —C(O)CH$_3$), benzoyl (Bz or —C(O)C$_6$H$_5$), and trimethylsilyl (TMS or —Si(CH$_3$)$_3$).

The term "protected hydroxy," as used herein, refers to a hydroxy group protected with a hydroxy protecting group, as defined above, including benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, 1,1-dimethyl-2-propenyl, 3-methyl-3-butenyl, allyl, benzyl, para-methoxybenzyldiphenylmethyl, triphenylmethyl(trityl), tetrahydrofuryl, methoxymethyl, methylthiomethyl, benzyloxymethyl, 2,2,2-triehloroethoxymethyl, 2-(trimethylsilyl)ethoxymethyl, methanesulfonyl, para-toluenesulfonyl, trimethylsilyl, triethylsilyl, triisopropylsilyl, and the like. Preferred hydroxyl protecting groups for the present invention are acetyl (Ac or —C(O)CH$_3$), benzoyl (Bz or —C(O)C$_6$H$_5$), and trimethylsilyl (TMS or —Si(CH$_3$)$_3$).

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the are described generally in T. H. Greene and P. G. M. Wuts, *Protective Groups in Organic Synthesis,* 3rd edition, John Wiley & Sons, New York (1999). Examples of amino protecting groups include, but are not limited to, t-butoxycarbonyl, 9-fluorenylmethoxycarbonyl, benzyloxycarbonyl, and the like.

The term "protected amino," as used herein, refers to an amino group protected with an amino protecting group as defined above.

The term "acyl" includes residues derived from acids, including but not limited to carboxylic acids, carbamic acids, carbonic acids, sulfonic acids, and phosphorous acids. Examples include aliphatic carbonyls, aromatic carbonyls, aliphatic sulfonyls, aromatic sulfinyls, aliphatic sulfinyls, aromatic phosphates and aliphatic phosphates.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series,* John Wiley & Sons, NY, 1986.

The term "protic solvent," as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protic solvents may be found in organic chemistry textbooks or in specialized monographs, for example: *Organic Solvents Physical Properties, and Methods of Purification,* 4th ed., edited by John A. Riddick et al., Vol. 1, in the *Techniques of Chemistry Series,* John Wiley & Sons, NY, 1986.

The term "oxidizing agent(s)," as used herein, refers to reagents useful for oxidizing the 3-hydroxyl of the macrolide ring to the 3-carbonyl. Oxidizing agents suitable in the present process are either Swern oxidation reagents (dimethyl sulfoxide and an electrophilic compound selected from dicyclohexylcarbodiimide, acetic anhydride, trifluoroacetic anhydride, oxalyl chloride, or sulfur trioxide), Dess Martin oxidation reagents, or Corey-Kim oxidation reagents. A preferred method of oxidation is the use of the Corey-Kim oxidation reagents N-chlorosuccinimide-dimethyl sulfide complex.

The term "palladium catalyst," as used herein, refers to optionally supported palladium(0) such as palladium metal, palladium on carbon, palladium on acidic, basic, or neutral alumina, and the like; palladium(0) complexes such as tetrakis(triphenylphosphine)palladium(0) tris(dibenzylideneacetone)dipalladium(0); palladium(II) salts such as palladium acetate or palladium chloride; and palladium(II) complexes such as allylpalladium(II) chloride dimer, (1,1'-bis(diphenylphosphino)ferrocene)-dichloropalladium(II), bis(acetato)bis(triphenylphosphine)palladium(II), and bis (acetonitrile)dichloropalladium(II).

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein.

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired bridged macrocyclic products of the present invention. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis,* 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995).

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters of the compounds formed by the process of the present invention which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to a compound of Formula I. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8:1-38(1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

This invention also encompasses pharmaceutical compositions containing, and methods of treating bacterial infections through administering, pharmaceutically acceptable prodrugs of compounds produced by the process of the present invention. For example, compounds having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of formula I. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy) ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including but not limited to ether, amine and carboxylic acid functionalities.

Suitable concentrations of reactants is 0.01M to 10M, typically 0.1M to 1M. Suitable temperatures include −10° C. to 250° C., typically −78° C. to 150° C., more typically −78° C. to 100° C., still more typically 0° C. to 100° C. Reaction vessels are preferably made of any material which does not substantial interfere with the reaction. Examples include glass, plastic, and metal. The pressure of the reaction can advantageously be operated at atmospheric pressure. The atmospheres includes, for example, air, for oxygen and water insensitive reactions, or nitrogen or argon, for oxygen or water sensitive reactions.

The term "in situ," as used herein, refers to use of an intermediate in the solvent or solvents in which the intermediate was prepared without removal of the solvent.

Unless otherwise defined, all technical and scientific terms used herein are accorded the meaning commonly known to one with ordinary skill in the art. All publications, patents, patent applications, and other references mentioned herein are hereby incorporated by reference in their entirety.

ABBREVIATIONS

Abbreviations which may be used in the descriptions of the schemes and the examples that follow are:
Ac for acetyl;
AIBN for azobisisobutyronitrile;
Bu₃SnH for tributyltin hydride;
CDI for carbonyldimidazole;
dba for dibenzylidene acetone;
dppb for diphenylphosphino butane or 1,4-bis(diphenylphosphino)butane;
DBU for 1,8-diazabicyclo[5.4.0]undec-7-ene;
DEAD for diethylazodicarboxylate;
DMAP for dimethylaminopyridine;
DMF for dimethyl formamide;
DPPA for diphenylphosphoryl azide;
EtOAc for ethyl acetate;
HPLC for high-pressure liquid chromatography;
MeOH for methanol;
NaN(TMS)₂ for sodium bis(trimethylsilyl)amide;
NMMO for N-methylmorpholine N-oxide;
TEA for triethylamine;
THF for tetrahydrofuran;
TPP or PPh₃ for triphenylphosphine;
MOM for methoxymethyl;
Boc for t-butoxycarbonyl;
Bz for benzyl;
Ph for phenyl;
POPd for dihydrogen dichlorobis(di-tert-butylphosphinito-KP)palladate(II);
TBS for tert-butyl dimethylsilyl; or
TMS for trimethylsilyl.

All other abbreviations used herein, which are not specifically delineated above, shall be accorded the meaning which one of ordinary skill in the art would attach.

Synthetic Methods

The process of the present invention can be better understood in view of the following schemes and methods.

The process of the present invention provides a method by which to bridge a macrocyclic compound which is characterized by two nucleophilic moieties with a bifunctional bridging reagent. The bifunctional bridging reagent is preferably characterized by its ability to form π-allyl metal complexes which undergo nucleophilic attack by the nucleophilic moieties present on or in the macrocyclic compound. It is understood that when the macrocyclic compounds useful in the process of the present invention possess more than two nucleophilic moieties, selective protection and deprotection of any nucleophilic moiety or moieties can enable one of ordinary skill in the art to direct the formation of any desired bridged macrocylic product of the present invention. Examples of selective protection and deprotection techniques which are well known in the art include, but are not limited to, those found in T. H. Greene and P. G. M. Wuts, *Protective Groups in Organic Synthesis*, 3rd edition, John Wiley & Sons, New York (1999).

The bifunctional nature of the bridging reagent of the present invention, under some conditions, can favor the formation of different bridge lengths. It is understood that the preferred bridging reagent of the formula

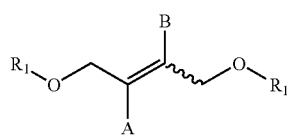

may produce either 4-carbon or 2-carbon bridged macrocyclic products through incorporation of various substitutions at A or B which will favor the formation of 4- or 2-carbon bridged macrocyclic products. Moreover, it is understood that the formation of a 2-carbon bridged macrocyclic product may be favored over the 4-carbon bridged macrocyclic product due to nucleophilic moieties which are in close proximity to each other. The formation of a 4-carbon bridged macrocyclic product and a 2-carbon macrocyclic product using the instant preferred bridging reagent is illustrated in Examples 2 and 4 respectively.

The process of the present invention may be performed either in a concerted or step-wise manner as exemplified in the ensuing examples.

In a preferred embodiment, the bridging reaction can take place in an aprotic solvent, at a temperature range of between 30° C. and 100° C., in the presence of a palladium catalyst and a ligand for a period of less than about 12 hours.

Bridging of a macrocyclic compound with a bifunctional bridging reagent preferably can take place in the presence of a palladium catalyst. Most palladium(0) catalysts are expected be effective in this process. Some palladium(II) catalysts, such as palladium(II) acetate, which are converted into a palladium(0) species in-situ by a phosphine, can be effective as well. See, for example, Beller et al. *Angew. Chem. Int. Ed. Engl.*, 1995, 34 (17), 1848. Preferable palladium catalysts for this reaction include, but are not limited to, palladium(II) acetate, tetrakis(triphenylphospine)palladium (0), tris(dibenzylideneacetone)dipalladium(0) (Pd$_2$(dba)$_3$), tetradi(benzylideneacetone)dipalladium and the like. Palladium on carbon and palladium(II) halide catalysts are less preferred than other palladium catalysts for this process. A preferred palladium catalyst for this process is a palladium(0) catalyst. A particularly preferred palladium catalyst for this process is Pd$_2$(dba)$_3$. In addition, the process of the present invention preferably can take place in the presence of a ligand. Preferably, the ligand can be a phosphine or an arsine. In a most preferred embodiment, the ligand is 1,4-bis(diphenylphosphino)butane (dppb).

The process of the present invention can preferably be carried out in an aprotic solvent, however protogenic organic solvents and mixtures of aprotic and protic solvents are also suitable for the process of the present invention. Suitable aprotic solvents include, but are not limited to, tetrahydrofuran, N,N-dimethylformamide, dimethyl sulfoxide, N-methyl-2-pyrrolidone, hexamethylphosphoric triamide, 1,2-dimethoxyethane, methyl-tert-butyl ether, heptane, acetonitrile, isopropyl acetate and ethyl acetate. Preferred aprotic solvents are tetrahydrofuran or toluene.

The instant conversion can be performed preferably at an elevated temperature between 30 and 100° C. A preferred temperature range is between 55° C. and 85° C. A most preferred temperature range for the instant alkylation process is between 60° C. and 75° C.

The instant alkylation process is generally conducted until at least 50% completion, preferably at least about 70% completion, typically until at least 95% completion. Preferably, the reaction time will be less than about 12 hours. A preferred reaction time range for the present alkylation process is less than about 8 hours. A most preferred reaction time range for the present alkylation process is less than about 7 hours.

All references cited herein, whether in print, electronic, computer readable storage media or other form, are expressly incorporated by reference in their entirety, including but not limited to, abstracts, articles, journals, publications, texts, treatises, internet web sites, databases, patents, and patent applications (whether published or unpublished).

EXAMPLES

The following examples represent exemplary conditions which demonstrate the versatility of the methodology and are not meant to be restricted to the modes and compounds or intermediates disclosed.

Example 1

Formation of 6,9 3-Carbon Bridged Erythromycin Derivative

Step 1a:

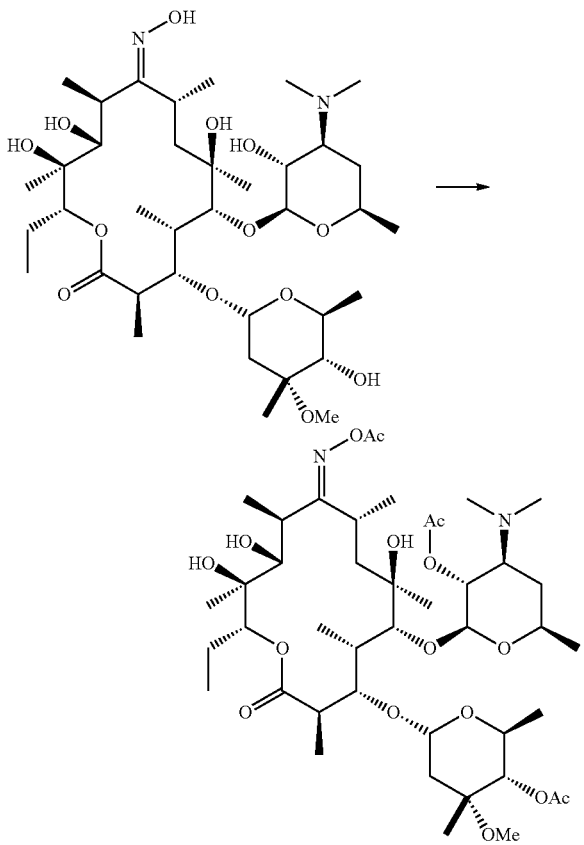

To a solution of erythromycin A oxime (74.9 g, 0.1 mol) in 400 ml THF was added acetic anhydride (35.9 ml, 0.38 mol), triethylamine (55.7 ml, 0.4 mol) and DMAP (3.7 g, 0.03 mol) at room temperature. The mixture was stirred at room temperature for 16 hours, condensed to ~200 ml, and diluted with 300 ml of ethyl acetate. The resulting mixture was washed with NaHCO$_3$ (Sat.) (500 ml×4) and brine (500 ml), and dried on anhydrous sodium sulfate. The solvent was evaporated in vacuo and the residue was recrystallized from ethyl acetate to give the desired product (78 g).

MS (ESI) m/z 875.46 (M+H)$^+$.

$^{13}$C NMR(CDCl$_3$): δ 178.5, 175.4, 170.6, 170.2, 168.2, 100.2, 96.1, 83.3, 79.3, 78.7, 75.2, 74.5, 72.9, 70.0, 67.6, 63.4, 63.2, 60.6, 49.5, 44.7, 40.9, 35.4, 31.8, 28.5, 22.8, 21.7, 21.6, 21.5, 21.3, 21.2, 21.1, 19.9, 18.6, 18.4, 16.7, 14.9, 14.4, 14.3, 10.8, 9.2.

Step 1b:

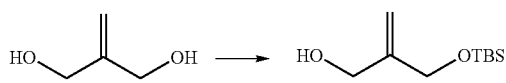

A suspension of NaH (1.26 g, 50 mmol) in THF (40 ml) was added to a solution of 2-methylene-1,3-propane diol (4.4 g, 50 mmol) in THF (30 ml). The mixture was stirred at room temperature for 45 minutess, to which was added a solution of tert-butyldimethylsilyl chloride (7.54 g, 50 mmol) in THF (30 ml). The resulting reaction mixture was stirred at room temperature for 1 hour, quenched with saturated NaHCO3 (200 ml), extracted with diethyl ether (150 ml×2), and the combined organic layers were dried over MgSO$_4$. The solvent was subsequently evaporated in vacuo and the residue was purified by flash chromatography (SiO$_2$ hexane:ethyl acetate/10:1) to give the desired product. (8.4 g)

$^1$H NMR (CDCl$_3$): δ 5.01 (s, 1H); 4.96 (s, 1H), 4.17 (s, 2H); 4.09 (s, 2H), 1.92 (bs, 1H), 0.83 (s, 9H), 0.00 (s 6H).

$^{13}$C NMR(CDCl$_3$): δ 152.9, 116.5, 70.5, 70.1, 31.3, 23.7, 0.0.

Step 1c:

To a solution of compound from step 1b (8.1 g, 40 mmol) in CH$_2$Cl$_2$ (100 ml) was added 6N NaOH (30 ml), di-tert-butyl dicarbonate (13.1 g, 60 mmol) and tetrabutylammoniahydrogensulfate (1.2 g, 3.5 mmol). The resulting reaction mixture was stirred at room temperature for overnight. The organic layer was separated, washed with NaHCO$_3$ (200 ml×3) and brine (200 ml), and dried over anhydrous MgSO$_4$. The solvent was subsequently evaporated in vacuo and the residue was purified by flash chromatography (SiO$_2$ hexane:ethyl acetate/96:4) to give the desired product. (6.8 g).

$^1$H NMR (CDCl$_3$): δ 5.17 (s, 1H); 5.08 (s, 1H), 4.50 (s, 2H); 4.11 (s, 2H), 1.41 (s, 9H), 0.84 (s, 9H), 0.00 (s 6H).

$^{13}$C NMR(CDCl$_3$): δ 153.8, 143.5, 113.6, 82.5, 67.6, 64.2, 38.2, 36.3, 18.8, −5.0.

Step 1d:

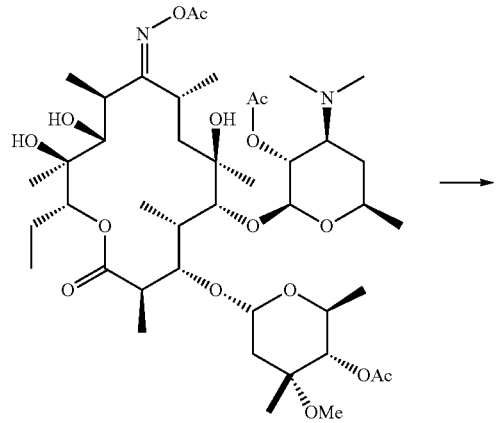

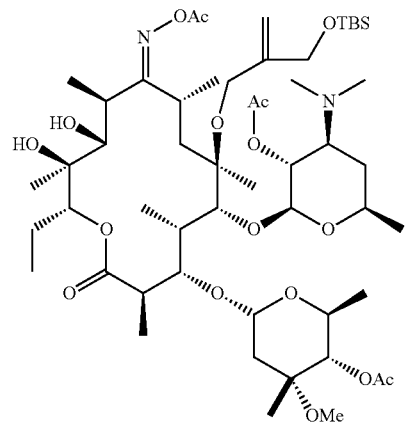

To a solution of erythromycin oxime 2',4",9-triacetate from Step 1a (22 g, 25 mmol), the compound from step 1c (9.1 g, 30 mmol), and dppb (853 mg, 2 mmol) in THF (250 ml), was added Pd$_2$(dba)$_3$ (916 mg, 1 mmol) under nitrogen. The mixture was refluxed for 15 hours, diluted with ethyl acetate (500 ml), washed with saturated NaHCO$_3$ (500 ml×2) and brine (500 ml), and dried over anhydrous Na$_2$SO$_4$. The solvent was subsequently removed in vacuo, and the residue was purified by flash chromatography (SiO$_2$ hexane:acetone/2:1) to give the desired product. (25 g)

MS (ESI) m/z 1059.65 (M+H)$^+$ $^{13}$C NMR(CDCl$_3$): δ 175.8, 173.9, 170.4, 170.1, 168.1, 143.1, 111.1, 99.4, 96.6, 79.8, 78.9, 78.5, 78.1, 77.4, 76.8, 74.3, 72.7, 72.2, 70.2, 68.0, 65.0, 63.6, 63.2, 49.2, 44.5, 40.8, 37.8, 37.0, 35.3, 31.1, 28.2, 26.0, 21.7, 21.5, 21.2, 20.9, 19.8, 19.7, 18.6, 18.3, 16.6, 16.3, 15.0, 10.6, 9.8, −5.4.

Step 1e:

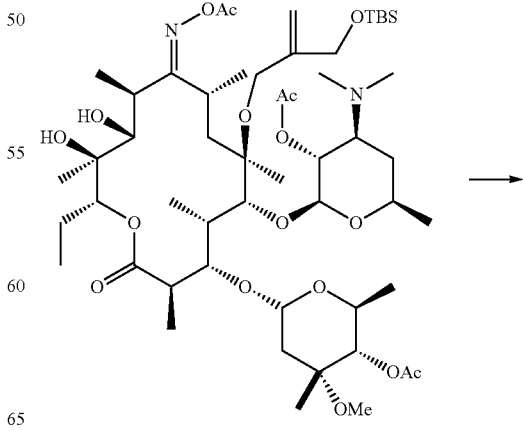

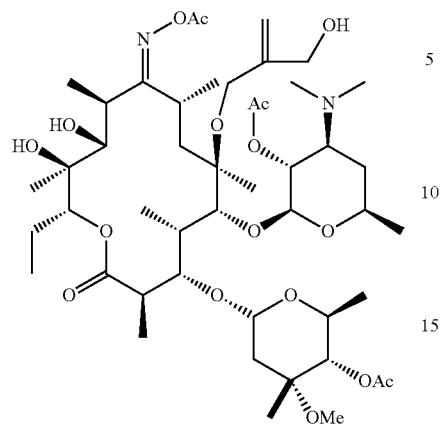

To a solution of compound from step 1d (2.65 g, 2.5 mmol) in THF (15 ml) and pyridine (1.5 ml) was added a stock solution of HF-pyridine in THF (7 ml, 8.5 mmol). The resulting reaction mixture was stirred at room temperature overnight, diluted with ethyl acetate (50 ml), and washed with saturated NaHCO$_3$ (50 ml×2). The washed extract was subsequently dried over anhydrous Na$_2$SO$_4$, the solvent was removed in vacuo, and the residue was purified by flash chromatography (SiO$_2$ hexane:acetone/2:1) to give the desired product. (2.1 g)

MS (ESI) m/z 945.51 (M+H)$^+$ $^{13}$C NMR (CDCl$_3$): δ 176.6, 175.3, 170.6, 170.3, 168.7, 146.3, 113.3, 99.7, 96.6, 80.2, 78.6, 77.6, 74.5, 72.9, 72.3, 70.2, 67.3, 65.2, 63.6, 63.4, 63.0, 49.4, 44.8, 41.0, 37.9, 37.0, 35.6, 34.7, 31.3, 29.5, 28.4, 21.9, 21.8, 21.6, 21.5, 21.3, 21.1, 20.1, 20.0, 18.7, 16.9, 16.6, 15.2, 10.7, 9.7.

Step 1f:

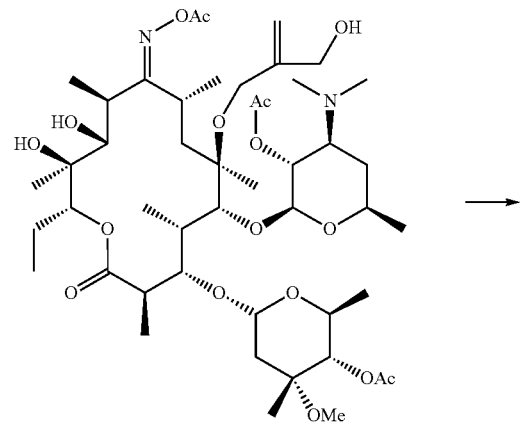

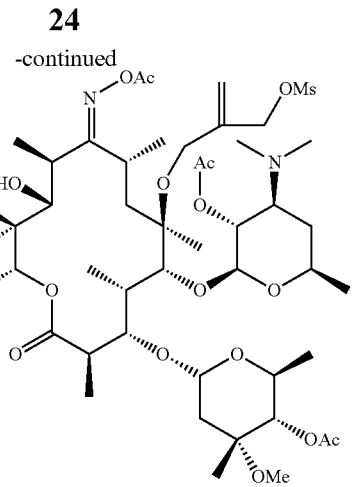

To a solution of the compound from step 1e (473 mg, 0.5 mmol) in CH$_2$Cl$_2$ (10 ml) was added triethyl amine (140 ul, 1 mmol) and methanesulfonic anhydride (131 mg, 0.75 mmol) at room temperature. The mixture was stirred at room temperature for 4 hours, washed with saturated NaHCO$_3$ (10 ml×2), and dried over anhydrous Na$_2$SO$_4$. The solvent was subsequently removed in vacuo, and the residue was purified by flash chromatography (SiO$_2$ hexane:acetone/2:1) to give the desired product. (500 mg).

MS (ESI) m/z 1023.52 (M+H)$^+$

Step 1g:

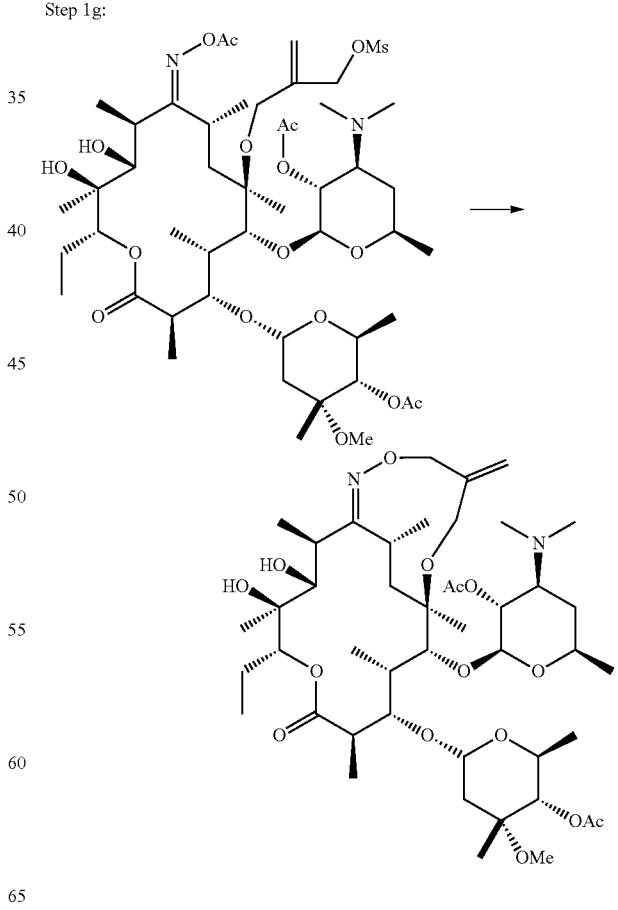

To a solution of the compound from step 1f (201 mg, 0.2 mmol) in CH$_2$Cl$_2$ (5 ml) was added 2N NaOH (5 ml) and tetrabutylammoniahydrogensulfate (39 mg, 0.1 mmol). The resulting reaction mixture was stirred at room temperature for 2 hours, diluted with CH$_2$Cl$_2$ (10 ml), and washed with saturated NaHCO$_3$ (15 ml×2). The washed solution was subsequently dried over anhydrous Na$_2$SO$_4$, the solvent was removed in vacuo, and the residue was purified by flash chromatography (SiO$_2$ hexane:acetone/2:1) to give the desired product. (123 mg).

MS (ESI) m/z 885.44 (M+H)$^+$ $^{13}$C NMR(CDCl$_3$): δ 175.9, 174.8, 170.6, 170.2, 143.1, 121.1, 99.8, 96.4, 80.9, 80.4, 78.8, 77.9, 74.5, 72.9, 72.3, 71.3, 67.2, 63.4, 63.3, 49.4, 44.6, 40.9, 38.2, 33.1, 31.8, 27.5, 25.5, 22.8, 21.8, 21.3, 21.1, 18.6, 18.0, 16.7, 14.3, 10.7, 9.5.

Example 2

Formation of 6-9 4-Carbon Bridged Erythromycin Derivatives

Step 2a:

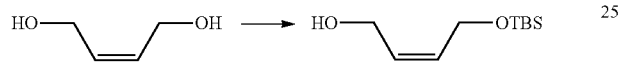

A suspension of NaH (1.26 g, 50 mmol) in THF (40 ml) was added to a solution of 2-butene-1,4-diol (4.4 g, 50 mmol) in THF (30 ml). The resulting reaction mixture was stirred at room temperature for 45 minutes and was added a solution of tert-butyldimethylsilyl chloride (7.54 g, 50 mmol) in THF (30 ml). The mixture was stirred at room temperature for 1 hour, quenched with saturated NaHCO$_3$ (200 ml), extracted with diethyl ether (150 ml×2), and the combined organic layers were dried over MgSO$_4$. The solvent was subsequently evaporated in vacuo and the residue was purified by flash chromatography (SiO$_2$ hexane:ethyl acetate/10:1) to give the desired product. (8.4 g)

$^1$H NMR (CDCl$_3$): δ 5.59 (m, 2H); 4.17 (d, 2H), 4.11 (d, 2H); 2.10 (bs, 1H), 0.82 (s, 9H), 0.00 (s 6H).

$^{13}$C NMR (CDCl$_3$): 6136.5, 135.3, 64.8, 64.1, 31.1, 23.6, 0.0

Step 2b:

To a solution of compound from step 2a (8.1 g, 40 mmol) in CH$_2$Cl$_2$ (100 ml) was added 6N NaOH (30 ml), di-tert-butyl dicarbonate (13.1 g, 60 mmol) and tetrabutylammoniahydrogensulfate (1.2 g, 3.5 mmol). The resulting reaction mixture was stirred at room temperature overnight. The organic layer was separated, washed with NaHCO$_3$ (200 ml×3) and brine (200 ml), and dried over anhydrous MgSO$_4$ The solvent was subsequently evaporated in vacuo and the residue was purified by flash chromatography (SiO$_2$ hexane:ethyl acetate/96:4) to give the desired product. (6.8 g).

$^1$H NMR (CDCl$_3$): δ 5.65 (m, 1H); 5.54 (m, 1H), 4.57 (d, 2H), 4.21 (d, 2H); 1.41 (s, 9H), 0.83 (s, 9H), 0.00 (s 6H).

$^{13}$C NMR (CDCl$_3$): δ 153.6, 134.4, 124.2, 82.4, 63.0, 59.8, 28.0, 26.1, 18.5, −5.0.

Step 2c:

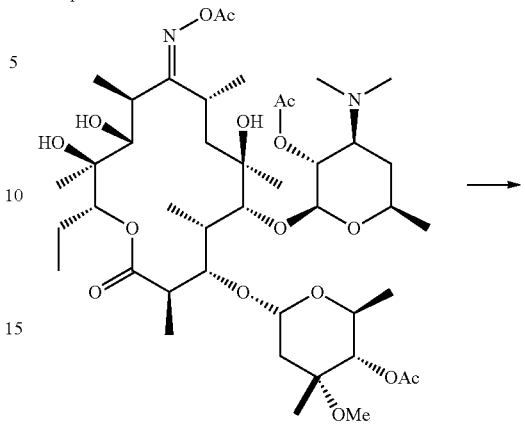

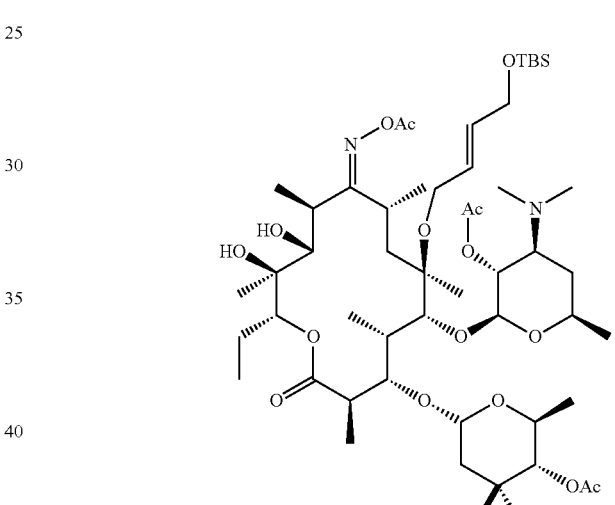

To a solution of erythromycin oxime 2',4'',9-triacetate from Step 1a (1.75 g, 2 mmol), the compound from step 2b (0.9 g, 3 mmol) and dppb (170 mg, 0.4 mmol) in THF (10 ml), was added Pd$_2$(dba)$_3$ (183 mg, 0.2 mmol) under nitrogen. The resulting reaction mixture was refluxed for 15 hours, after which the reaction mixture was diluted with ethyl acetate (50 ml), washed with saturated NaHCO$_3$ (50 ml×2) and brine (50 ml), and dried over anhydrous Na$_2$SO$_4$. The solvent was removed in vacuo, and the residue was purified by flash chromatography (SiO$_2$ hexane:acetone/2:1) to give the desired product. (1.5 g)

MS (ESI) m/z 1059.65 (M+H)$^+$ $^{13}$C NMR (CDCl$_3$): δ 176.5, 174.7, 170.6, 170.3, 168.9, 132.5, 127.6, 99.7, 96.4, 79.3, 79.0, 78.7, 78.5, 77.5, 76.8, 74.5, 72.9, 72.3, 69.7, 67.2, 64.7, 63.6, 63.5, 63.4, 49.4, 44.5, 42.0, 38.0, 37.8, 35.5, 34.4, 32.8, 32.4, 32.1, 29.5, 26.3, 26.2, 22.9, 21.8, 21.4, 21.3, 21.1, 20.2, 19.0, 18.7, 18.6, 16.8, 16.2, 15.2, 10.9, 9.5, −5.0, −5.1.

Step 2d:

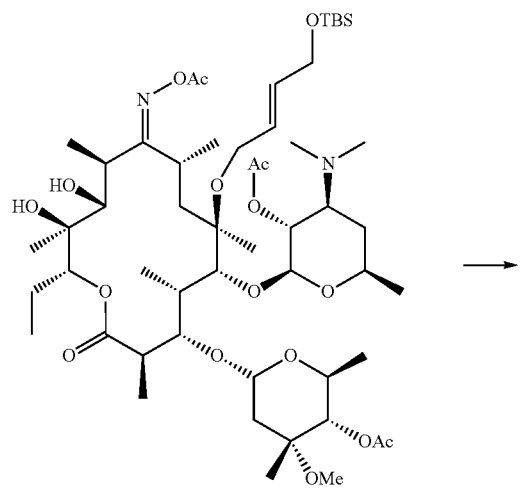

Step 2e:

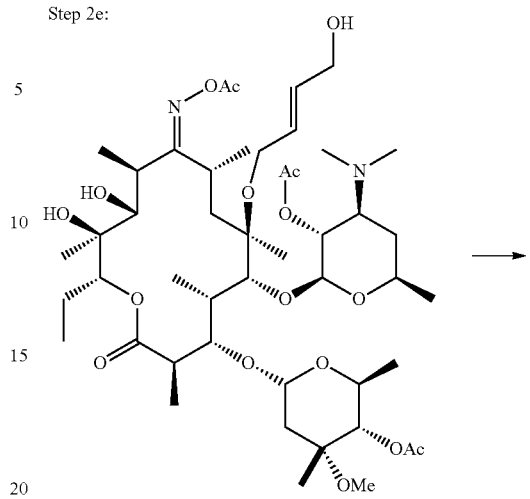

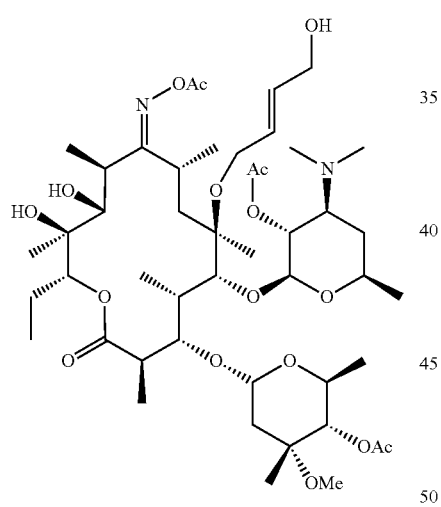

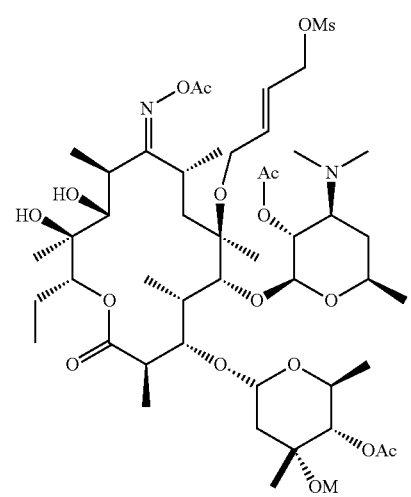

To a solution of compound from step 2c (2.65 g, 2.5 mmol) in THF (15 ml) and pyridine (1.5 ml) was added a stock solution of HF-pyridine in THF (7 ml, 8.5 mmol). The resulting reaction mixture was stirred at room temperature overnight, after which the reaction mixture was diluted with ethyl acetate (50 ml), washed with saturated NaHCO$_3$ (50 ml×2), dried over anhydrous Na$_2$SO$_4$. The solvent was subsequently removed in vacuo and the residue was purified by flash chromatography (SiO$_2$ hexane:acetone/2:1) to give the desired product. (2.1 g) MS (ESI) m/z 945.46 (M+H)$^+$ $^{13}$C NMR (CDCl$_3$): δ 177.6, 175.9, 171.0, 170.4, 168.2, 132.4, 128.1, 99.6, 96.8, 79.6, 78.5, 77.4, 72.2, 70.2, 67.4, 64.5, 63.8, 63.7, 49.6, 44.3, 40.8, 38.2, 37.2, 35.6, 34.4, 31.4, 28.6, 22.0, 21.7, 21.5, 19.9, 19.3, 19.2, 16.7, 16.3, 15.4, 11.2, 9.8.

To a solution of the compound from step 2d (473 mg, 0.5 mmol) in CH$_2$Cl$_2$ (10 ml) was added triethyl amine (140 ul, 1 mmol) and methanesulfonic anhydride (131 mg, 0.75 mmol) at room temperature. The resulting reaction mixture was stirred at room temperature for 4 hours, after which the reaction mixture was washed with saturated NaHCO$_3$ (10 ml×2) and dried over anhydrous Na$_2$SO$_4$. The solvent was subsequently removed in vacuo, and the residue was purified by flash chromatography (SiO$_2$ hexane:acetone/2:1) to give the desired product. (500 mg).

MS (ESI) m/z 1023.55 (M+H)$^+$

Step 2f:

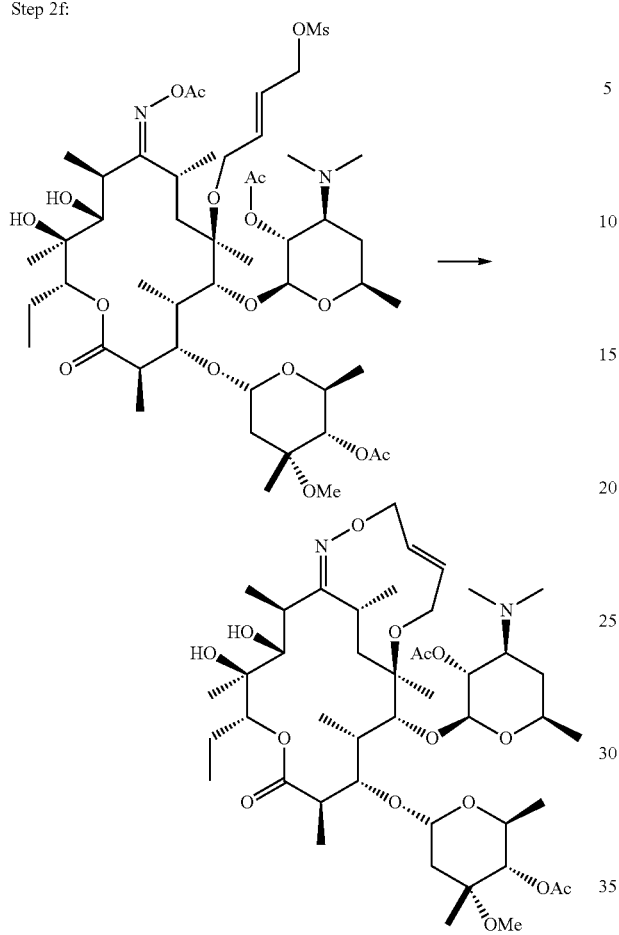

To a solution of the compound from step 2e (201 mg, 0.2 mmol) in CH$_2$Cl$_2$ (5 ml) was added 2N NaOH (5 ml) and tetrabutylammoniahydrogensulfate (39 mg, 0.1 mmol). The resulting mixture was stirred at room temperature for 2 hours, after which the reaction mixture was diluted with CH$_2$Cl$_2$ (10 ml), washed with saturated NaHCO$_3$ (15 ml×2), and dried over anhydrous Na$_2$SO$_4$, the solvent was removed in vacuo, and the residue was purified by flash chromatography (SiO$_2$ hexane:acetone/2:1) to give the desired product. (150 mg).
MS (ESI) m/z 885.49 (M+H)$^+$ Example 3

Formation of 6-11 3-Carbon Bridged Erythromycin Derivatives

Step 3a

To a solution of 2-methylene-1,3-propane diol (5.28 g, 0.06 mmol) and di-tert-butyl dicarbonate (35 g, 0.16 mol) in 150 ml of dichloromethane was added 6N NaOH (70 ml) and TBAHS (3.4 g, 10 mmol). The mixture was stirred at room temperature overnight. The organic layer was separated, washed with NaHCO$_3$ (200 ml×3) and brine (200 ml), dried over anhydrous MgSO$_4$, and concentrated in vacuo to give the desired product.

$^1$H NMR (CDCl$_3$): δ 5.20 (s, 2H); 4.44 (s, 4H); 1.18 (s, 18H).

$^{13}$C NMR(CDCl$_3$): δ 153.28, 138.50, 117.27, 82.27, 66.91, 27.83.

Step 3b

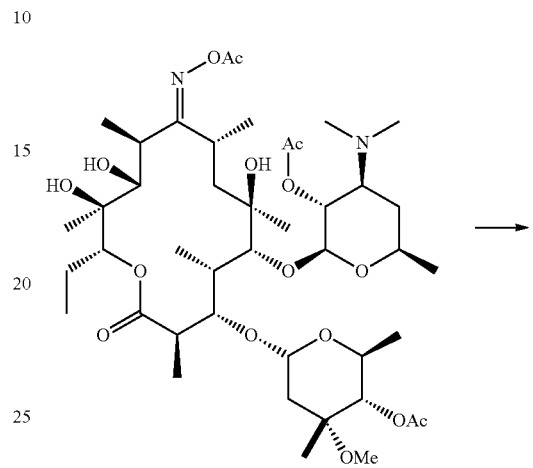

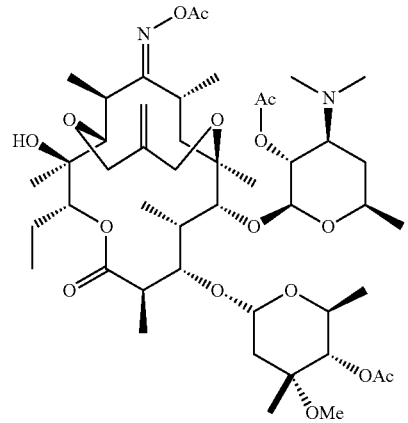

To a solution of erythromycin oxime 2',4",9-triacetate from Step 1a (112 g, 128 mmol), the compound from step 3a (44.3 g, 154 mmol) and dppb (1.71 g, 4 mmol) in THF (500 ml), was added Pd$_2$(dba)$_3$ (1.83 g, 2 mmol) under nitrogen. The mixture was refluxed for 5 hours and subsequently concentrated in vacuo. The residue was purified by flash chromatography (SiO$_2$ hexane:acetone/2:1) to give the desired product (110 g).

MS (ESI) m/z 927.64 (M+H)$^+$.

$^{13}$C NMR(CDCl$_3$): δ 176.5, 175.9, 170.7, 170.1, 169.9, 141.6, 124.7, 100.4, 96.0, 79.1, 78.7, 78.2, 78.0, 77.4, 76.5, 73.5, 73.0, 72.4, 72.1, 67.8, 66.1, 63.4, 63.3, 49.6, 44.1, 41.2, 40.9, 37.3, 35.4, 35.1, 31.3, 29.5, 28.5, 27.1, 23.4, 21.7, 21.3, 21.1, 20.9, 20.3, 18.8, 18.3, 17.4, 15.7, 13.4, 12.7, 8.6.

Example 4

Formation of 9a-11 2-Carbon Bridged Azithromycin Derivatives

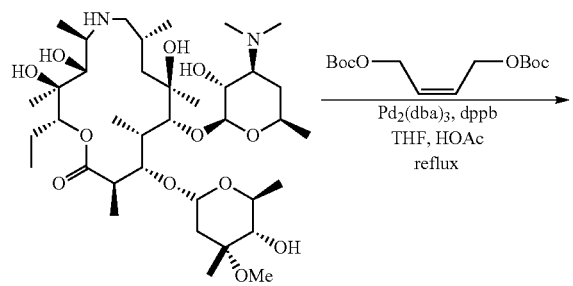

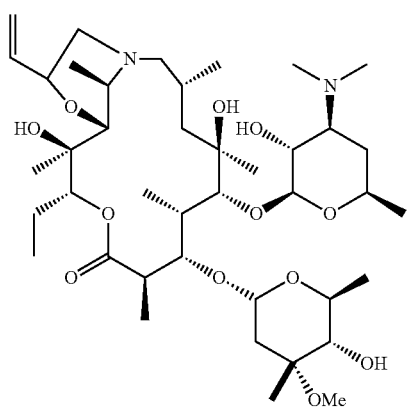

To a solution of desmethyl azithromycin (2.94 g, 4 mmol), BocOCH$_2$CH=CHCH$_2$OBoc (1.5 g, 5.2 mmol) and dppb (171 mg, 0.4 mmol) in THF (50 ml) and acetic acid, was added Pd$_2$(dba)$_3$ (183 mg, 0.2 mmol) under nitrogen. The mixture was refluxed for 5 hours and subsequently concentrated in vacuo. The residue was purified by flash chromatography (SiO$_2$ hexane:acetone/2:1) to give a mixture of stereoisomers (2.4 g).

MS (ESI) m/z: 787.87 (M+H).

$^{13}$C-NMR (100 MHz, CDCl$_3$): δ 175.9, 136.1, 116.6, 103.5, 96.9, 84.9, 81.1, 78.7, 78.3, 77.2, 76.3, 74.1, 73.4, 73.0, 71.3, 68.9, 66.0, 65.8, 64.2, 56.6, 49.8, 49.6, 45.0, 41.9, 40.6, 39.6, 35.6, 29.1, 27.1, 27.0, 21.8, 21.6, 18.9, 17.1, 15.5, 10.9, 9.9, 5.5.

Example 5

Formation of 9a-11 3-carbon Bridged Azithromycin

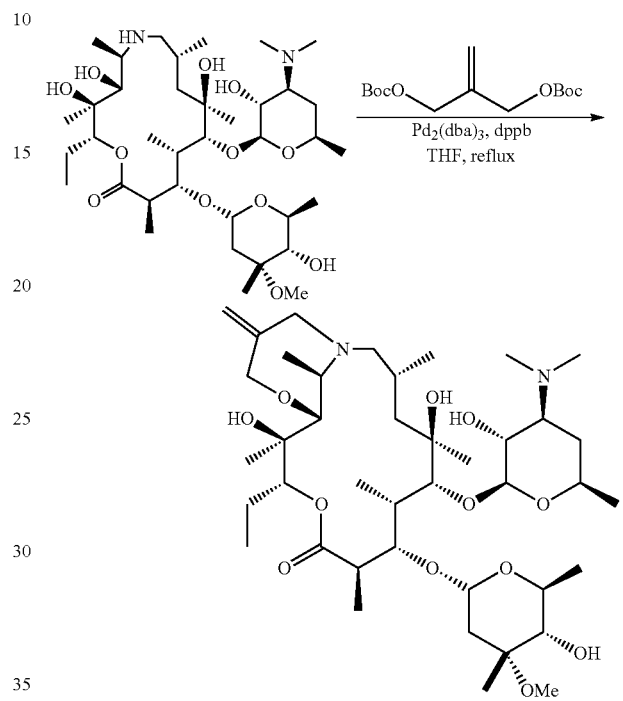

To a solution of desmethyl azithromycin (14.7 g, 20 mmol), the compound from step 3a (6.92 g, 24 mmol) and dppb (512 mg, 1.2 mmol) in THF (200 ml), is added acetic acid (1.14, 20 mmol) and Pd$_2$(dba)$_3$ (550 mg, 0.5 mmol) under nitrogen. The mixture is refluxed for 4 hours, diluted with ethyl acetate (250 ml), washed with saturated NaHCO$_3$ (200 ml×2) and brine (200 ml), and dried over anhydrous Na$_2$SO$_4$. The solvent was removed in vacuo, and the residue was purified by flash chromatography (SiO$_2$, 2M NH$_3$ in methanol/CH$_2$Cl$_2$=5/95) to give the title compound (11 g).

MS (ESI) m/z 787.55 (M+H)$^+$ $^{13}$C NMR (CDCl$_3$): δ 177.1, 145.6, 114.3, 103.2, 95.8, 84.4, 83.7, 79.6, 78.3, 77.2, 74.3, 74.2, 74.0, 73.2, 71.3, 69.6, 69.0, 66.0, 65.9, 64.5, 54.5, 53.7, 49.7, 45.4, 42.6, 41.2, 40.6, 35.4, 29.2, 27.2, 22.3, 21.9, 21.7, 21.2, 18.6, 16.7, 16.1, 11.1, 9.8, 7.6.

Further examples of the process of the present invention are described in U.S. patent application Ser. Nos. 10/429,485, 10/436,622, 10/205,357, and 10/205,018; and U.S. Pat. No. 6,645,941, which are incorporated by reference in their entirety.

Although the invention has been described in detail with respect to various preferred embodiments it is not intended to be limited thereto, but rather those skilled in the art will recognize that variations and modifications may be made therein which are within the spirit of the invention and the scope of the appended claims.

What is claimed is:
1. A process comprising the step of reacting a macrocyclic compound characterized by at least two nucleophilic moieties with a bifunctional bridging component characterized by its ability to form π-allyl metal complex in the presence of catalyst, whereby each of two nucleophilic moieties of the macrocyclic compound reacts with said bifunctional bridging component, thereby achieving a bridged macrocyclic product.

2. The process of claim 1, wherein the macrocyclic compound is a macrolide antibiotic.

3. The process of claim 1, wherein the macrocyclic compound is an erythromycin derivative.

4. The process of claim 3, wherein the erythromycin derivative is azithromycin, desmethyl azithromycin, roxithromycin, clarithromycin, telithromycin, or cethromycin.

5. The process of claim 1, wherein the macrocyclic compound is selected from:

I
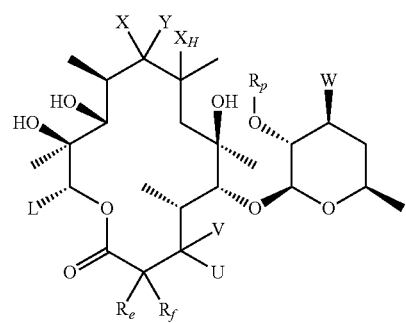

II
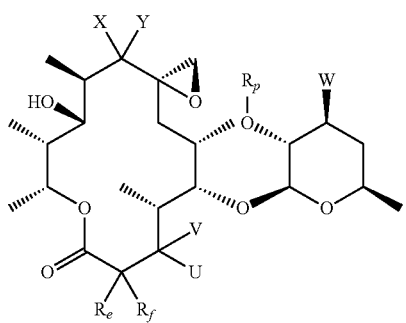

III
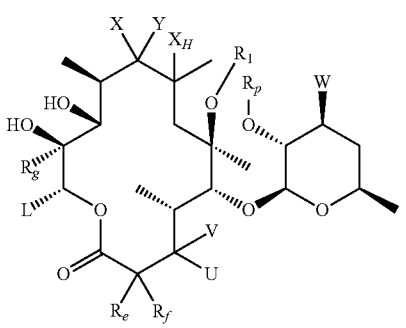

IV
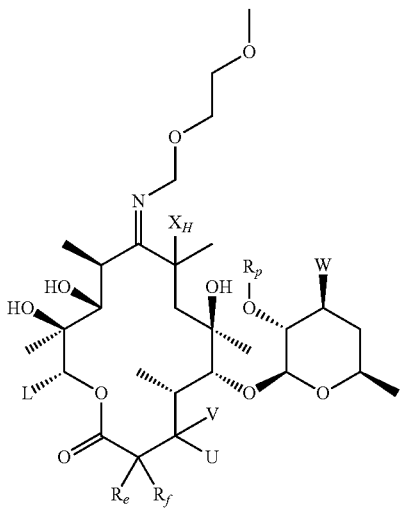

V
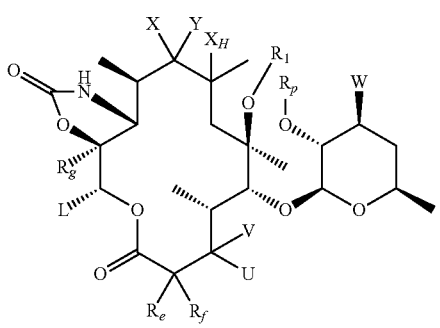

VI
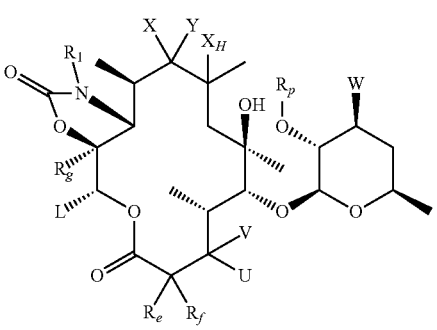

VII
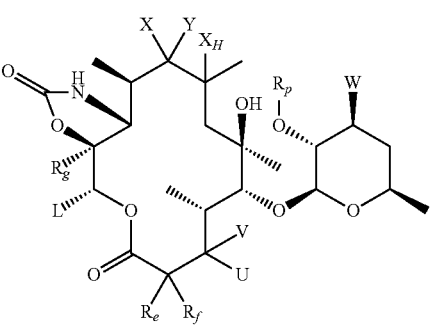

-continued

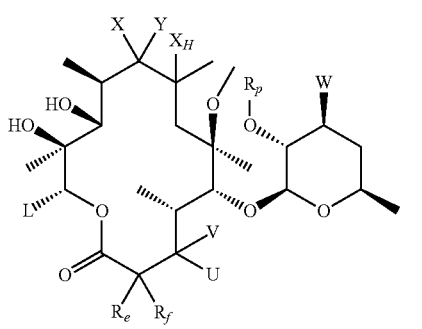

VIII

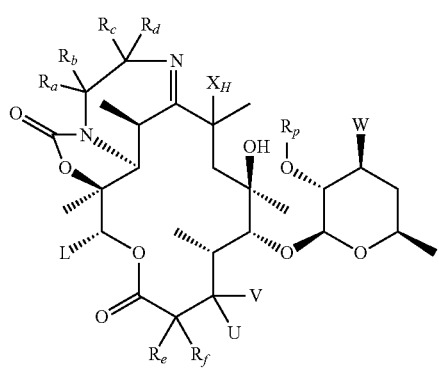

IX

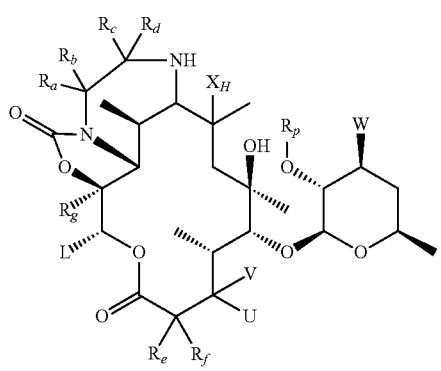

X

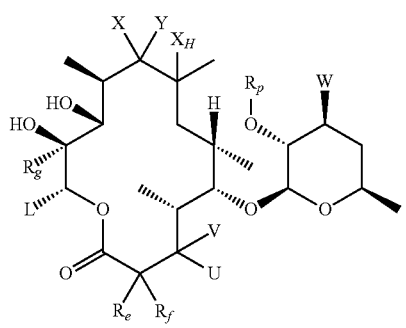

XI

-continued

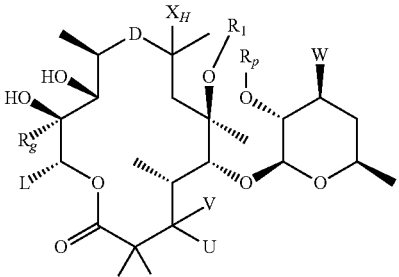

XII

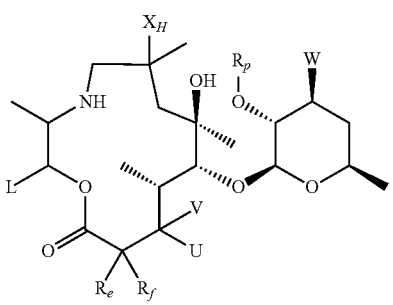

XIII

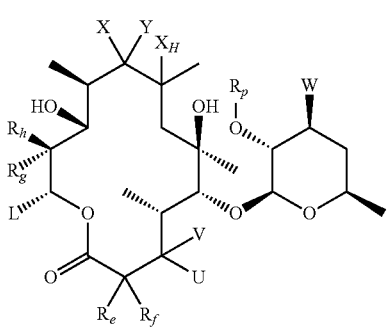

XIV wherein
D is selected from —NHCH$_2$—, —NHCHR$_1$—, —NHCR$_3$R$_4$—, —NR$_1$CH$_2$—, —NHC(O)—, —NR$_1$C(O)—, —NHC(S)—, or —NR$_1$C(S)—;

Each R$_1$ is independently selected from hydrogen, deuterium, a substituted or unsubstituted, saturated or unsaturated aliphatic group, a substituted or unsubstituted, saturated or unsaturated alicyclic group, a substituted or unsubstituted aromatic group, a substituted or unsubstituted heteroaromatic group, saturated or unsaturated heterocyclic group;

R$_3$ and R$_4$ is independently selected from the group consisting of hydrogen, acyl, a substituted or unsubstituted, saturated or unsaturated aliphatic group, a substituted or unsubstituted, saturated or unsaturated alicyclic group, a substituted or unsubstituted aromatic group, a substituted or unsubstituted heteroaromatic group, saturated or unsaturated heterocyclic group; or can be taken together with the nitrogen atom to which they are attached to form a substituted or unsubstituted heterocyclic or heteroaromatic ring;

L is selected from hydrogen, a substituted or unsubstituted, saturated or unsaturated aliphatic group, a substituted or unsubstituted, saturated or unsaturated alicyclic group, a substituted or unsubstituted aromatic group, a substituted or unsubstituted heteroaromatic group, or a substituted or unsubstituted heterocyclic group;

one of U or V is hydrogen and the other is independently selected from the group consisting of: $R_1$, $OR_1$, $OC(O)R_1$, $OC(O)NR_3R_4$, $S(O)_nR_1$,

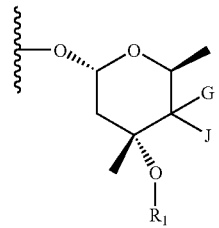

or other carbohydrate or sugar moiety;
  or U and V, taken together with the carbon atom to which they are attached, are C=O;
  or UV and $R_eR_f$, taken together with the carbon atoms to which they are attached, are —C($R_1$)=CH—;
  one of J or G is hydrogen and the other is selected from: $R_1$, $OR_1$, or $NR_3R_4$;
  or J and G, taken together with the carbon atom to which they are attached, are selected from: C=O, C=$NR_1$, C=$NOR_1$, C=NO(CH$_2$)$_m$R$_1$, C=NNHR$_1$, C=NNHCOR$_1$, C=NNHCONR$_3$R$_4$, C=NNHS(O)$_n$R$_1$, or C=N—N=CHR$_1$;
  $R_a$, $R_b$, $R_c$, and $R_d$ are independently selected from —$R_1$, —$OR_1$, —$S(O)_nR_1$, —$C(O)OR_1$, —$OC(O)R_1$, —$OC(O)OR_1$, —$C(O)R_1$, —$C(O)NH$—$R_1$, —$NHC(O)$—$R_1$, —$N(R_3)(R_4)$, —$NHC(O)$—$OR_1$, —$NHC(O)NH$—$R_1$, or —$OC(O)NH$—$R_1$;
  or $R_a$ and $R_b$, $R_a$ and $R_c$, $R_a$ and $R_d$, $R_b$ and $R_c$, $R_b$ and $R_d$, or $R_c$ and $R_d$, taken together with the carbon atom or atoms to which they are attached, are selected from substituted or unsubstituted alicyclic or substituted or unsubstituted heterocyclic;
  one of $R_e$ and $R_f$ is selected from hydrogen or methyl, and the other is independently selected from halogen, deuterium, or $R_1$;
  $R_h$ is hydroxy;
  $R_g$ is selected from hydrogen, a substituted or unsubstituted, saturated or unsaturated aliphatic group, a substituted or unsubstituted, saturated or unsaturated alicyclic group, a substituted or unsubstituted aromatic group, a substituted or unsubstituted heteroaromatic group, or a substituted or unsubstituted heterocyclic group;
  or $R_g$ and $R_h$, taken together with the carbon atom to which they are attached, are selected from an epoxide, a carbonyl, a substituted or unsubstituted olefin, a substituted or unsubstituted alicyclic, a substituted or unsubstituted heterocyclic;
  W is $NR_3R_4$;
  one of X and Y is hydrogen, substituted or unsubstituted aliphatic, and the other is independently selected from: hydroxy, —SH, —$NH_2$, or —$NR_1H$;
  or X and Y, taken together with the carbon atom to which they are attached, are selected from: C=O, C=$NR_1$, C=$NOR_1$, C=NO(CH$_2$)$_m$R$_1$, C=NNHR$_1$, C=NNHCOR$_1$, C=NNHCONR$_3$R$_4$, C=NNHS(O)$_n$R$_1$, or C=N—N=CHR$_1$;
  $R_p$ is selected from hydrogen, acyl, silane, or a hydroxy protecting group;
  $X_H$ is selected from hydrogen or halogen;
  m is an integer; and
  n is 0, 1, or 2.

6. The process of claim 5, wherein, for the macrocylic compound, L is ethyl.

7. The process of claim 5, wherein, for the macrocylic compound, one of X and Y is hydrogen and the other is selected from hydroxy or amino.

8. The process of claim 5, wherein, for the macrocylic compound, X and Y, taken together with the carbon atom to which they are attached, are selected from the group consisting of: C=O, C=NH, C=N—OH, or C=N—$NH_2$.

9. The process of claim 5, wherein, for the macrocylic compound, $R_g$ is methyl.

10. The process of claim 5, wherein, for the macrocylic compound, $R_e$ is hydrogen and $R_f$ is selected from methyl, allyl, or propargyl.

11. The process of claim 5, wherein, for the macrocylic compound, one of U and V is hydrogen and the other is selected from —OH or —O-cladinose.

12. The process of claim 5, wherein, for the macrocylic compound, U and V, taken together with the carbon atom to which they are attached, are C=O.

13. The process of claim 1 wherein each of the two nucleophilic moieties is alkylated by a functional group of the bridging component.

* * * * *